(12) United States Patent
Coghlan et al.

(10) Patent No.: US 6,380,207 B2
(45) Date of Patent: Apr. 30, 2002

(54) GLUCOCORTIOCOID-SELECTIVE ANTIINFLAMMATORY AGENTS

(75) Inventors: Michael J. Coghlan, Grayslake, IL (US); James P. Edwards, San Diego; Todd K. Jones, Solana Beach, both of CA (US); Michael E. Kort, Lake Bluff, IL (US)

(73) Assignees: Abbott Laboratories, Abbott Park, IL (US); Ligand Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/023,913

(22) Filed: Feb. 13, 1998

(51) Int. Cl.$^7$ .................. A61K 31/4741; C07D 491/02
(52) U.S. Cl. ................. 514/285; 546/76; 546/62; 546/61
(58) Field of Search ............... 514/285; 546/62, 546/61, 76

(56) References Cited

U.S. PATENT DOCUMENTS

| | | | |
|---|---|---|---|
| 5,688,808 A | 11/1997 | Jones et al. | 514/285 |
| 5,688,810 A | 11/1997 | Jones et al. | 514/311 |
| 5,693,133 A | 12/1997 | Largent et al. | 106/284.06 |
| 5,693,646 A | 12/1997 | Jones et al. | 514/285 |
| 5,693,647 A | 12/1997 | Jones et al. | 514/285 |
| 5,696,127 A | 12/1997 | Jones et al. | 514/285 |
| 5,696,130 A | 12/1997 | Jones et al. | 514/291 |

FOREIGN PATENT DOCUMENTS

WO 9619458 6/1996

OTHER PUBLICATIONS

Berge, S.M. et al., Journal Pharmaceutical Sciences, 1977, 66:1–19.

Edwards, J.P. et al. "5–Aryl–1,2–dihydro–5H–chromeno[3,4–f]quinolines as Potent, Orally Active, Nonsteroidal Progesterone Receptor Agonishts: The Effect of D–Ring Substitutuents," *J. Med. Chem.*, 41 (1998) 303–310 Anal. Biochem., 1970, 37, 244–252.

*Primary Examiner*—Charanjit S. Aulakh
(74) *Attorney, Agent, or Firm*—Schwegman, Lundberg, Woessner & Kluth, P.A.

(57) ABSTRACT

Compounds having Formula I

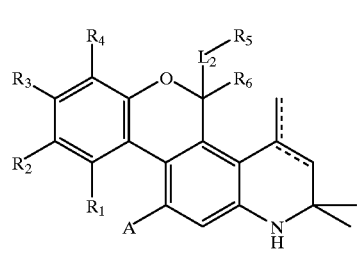

are useful for partially or fully antagonizing, repressing, agonizing, or modulating the glucocorticoid receptor in a mammal and treating immune, autoimmune and inflammatory diseases in a mammal. Also disclosed are pharmaceutical compositions comprising compounds of Formula I and methods of inhibiting immune or autoimmune diseases in a mammal.

6 Claims, No Drawings

GLUCOCORTIOCOID-SELECTIVE ANTIINFLAMMATORY AGENTS

TECHNICAL FIELD

The present invention relates to glucocorticoid receptor-selective benzopyrano[3,4-f]quinolines that are useful for treating immune or autoimmune diseases, to pharmaceutical compositions comprising these compounds, and to methods of inhibiting inflammation, inflamatory disease, immune, and autoimmune diseases in a mammal.

BACKGROUND OF THE INVENTION

Intracellular receptors (IR's) are a class of structurally related proteins involved in the regulation of gene expression. The steroid hormone receptors are a subset of this superfamily whose natural ligands are typically comprised of endogenous steroids such as estradiol, progesterone, and cortisol. Man-made ligands to these receptors play an important role in human health and, of these receptors, the glucocorticoid receptor (GR) has an essential role in regulating human physiology and immune response. Steroids which interact with GR have been shown to be potent antiinflammatory agents. Despite this benefit, steroidal GR ligands are not selective. Side effects associated with chronic dosing are believed to be the result of cross-reactivity with other steroid receptors such as estrogen, progesterone, androgen, and mineralocorticoid receptors which have somewhat homologous ligand binding domains.

Selective GR repressors, agonists, partial agonists and antagonists of the present disclosure can be used to influence the basic, life-sustaining systems of the body, including carbohydrate, protein and lipid metabolism, and the functions of the cardiovascular, kidney, central nervous, immune, skeletal muscle, and other organ and tissue systems, In this regard, GR modulators have proven useful in the treatment of inflammation, tissue rejection, autoimmunity, various malignancies, such as leukemias and lymphomas, Cushing's syndrome, acute adrenal insufficiency, congenital adrenal hyperplasia, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, stroke and spinal cord injury, hypercalcemia, hypergylcemia, acute adrenal insufficiency, chronic primary adrenal insufficiency, secondary adrenal insufficiency, congenital adrenal hyperplasia, cerebral edema, thrombocytopenia, and Little's syndrome.

GR modulators are especially useful in disease states involving systemic inflammation such as inflammatory bowel disease, systemic lupus erythematosus, polyartitis nodosa, Wegener's granulomatosis, giant cell arteritis, rheumatoid arthritis , osteoarthritis, hay fever, allergic rhinitis, urticaria, angioneurotic edema, chronic obstructive pulmonary disease, asthma, tendonitis, bursitis Crohn's disease, ulcerative colitis, autoimmune chronic active hepatitis, organ transplantation, hepatitis, and cirrhosis. GR active compounds have also been used as immunostimulants and repressors, and as wound healing and tissue repair agents.

GR modulators have also found use in a variety of topical diseases such as inflammatory scalp alopecia, panniculitis, psoriasis, discoid lupus erythematosus, inflamed cysts, atopic dermatitis, pyoderma gangrenosum, pemphigus vulgaris, bullous pemphigoid, systemic lupus erythematosus, dermatomyositis, herpes gestationis, eosinophilic fasciitis, relapsing polychondritis inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform, cutaneous T-cell lymphoma.

Selective antagonists of the glucocorticoid receptor have been unsuccessfully pursued for decades. These agents would potentially find application in several disease states associated with Human Immunodeficiency Virus (HIV), cell apoptosis, and cancer including, but not limited to, Kaposi's sarcoma, immune system activation and modulation, desensitization of inflammatory responses, IL-1 expression, anti-retroviral therapy, natural killer cell development, lymphocytic leukemia, and treatment of retinitis pigmentosa. Cogitive and behavioral processes are also susceptible to glucocorticoid therapy where antagonists would potentially be useful in the treatment of processes such as cognitive performance, memory and learning enhancement, depression, addiction, mood disorders, chronic fatigue syndrome, schizophrenia, stroke, sleep disorders, and anxiety.

SUMMARY OF THE INVENTION

In one embodiment of the present invention are compounds represented by Formula I

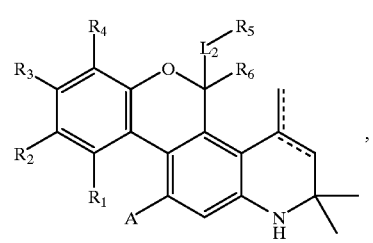

or pharmaceutically acceptable salts or prodrugs thereof, where the symbol - - - - represents a single or double bond, provided that no two double bonds are in adjacent positions;

A is —$L_1$—$R_A$ where $L_1$ is selected from
(1) a covalent bond,
(2) —O—,
(3) —S(O)$_t$— where t is 0, 1, or 2,
(4) —C(X)—,
(5) —NR$_7$— where R$_7$ is selected from
  (a) hydrogen,
  (b) aryl
  (c) cycloalkyl of three to twelve carbons,
  (d) alkanoyl where the alkyl part is one to twelve carbons,
  (e) alkoxycarbonyl where the alkyl part is one to twelve carbons,
  (f) alkoxycarbonyl where the alkyl part is one to twelve carbons and is substituted by 1 or 2 aryl groups,
  (g) alkyl of one to twelve carbons,
  (h) alkyl of one to twelve carbons substituted with 1 or 2 substituents independently selected from aryl or cycloalkyl of three to twelve carbons,
  (i) alkenyl of three to twelve carbons, provided that a carbon of a carbon-carbon double bond is not attached directly to nitrogen,
  (j) alkynyl of three to twelve carbons, provided that a carbon of a carbon-carbon triple bond is not attached directly to nitrogen, (6) —$NR_8C(X)NR_9$— where X is O or S and $R_8$ and $R_9$ are independently selected from
  (a) hydrogen,
  (b) aryl,
  (c) cycloalkyl of three to twelve carbons,
  (d) alkyl of one to twelve carbons,
  (e) alkyl of one to twelve carbons substituted with 1 or 2 substituents independently selected from aryl or cycloalkyl of three to twelve carbons,
  (f) alkenyl of three to twelve carbons,
    provided that a carbon of a carbon-carbon double bond is not attached directly to nitrogen,
  (g) alkynyl of three to twelve carbons,
    provided that a carbon of a carbon-carbon triple bond is not attached directly to nitrogen,
(7) —X'C(X)— where X is previously defined and X' is O or S,
(8) —C(X)X'—,
(9) —X'C(X)X''— where X and X' are previously defined and X'' is O or S,
  provided that when X is O, at least one of X' or X'' is O,
(10) —$NR_8C(X)$—,
(11) —$C(X)NR_8$—,
(12) —$NR_8C(X)X'$—,
(13) —$X'C(X)NR_8$—,
(14) —$SO_2NR_8$—,
(15) —$NR_8SO_2$—, and
(16) —$NR_8SO_2NR_9$— where (6)–(16) are drawn with their right ends attached to $R_A$ and $R_A$ is selected from
(1) —OH,
(2) —OG where G is a —OH protecting group,
(3) —SH,
(4) —CN,
(5) halo,
(6) haloalkoxy of one to twelve carbons,
(7) perfluoroalkoxy of one to twelve carbons,
(8) —CHO,
(9) —$NR_7R_{7'}$ where $R_7$ is defined previously and $R_{7'}$ is selected from
  (a) hydrogen,
  (b) aryl,
  (c) cycloalkyl of three to twelve carbons,
  (d) alkanoyl where the alkyl part is one to twelve carbons,
  (e) alkoxycarbonyl where the alkyl part is one to twelve carbons,
  (f) alkoxycarbonyl where the alkyl part is one to twelve carbons and is substituted by 1 or 2 aryl groups,
  (g) alkyl of one to twelve carbons,
  (h) alkyl of one to twelve carbons substituted with 1 or 2 substituents independently selected from aryl or cycloalkyl of three to twelve carbons,
  (i) alkenyl of three to twelve carbons,
    provided that a carbon of a carbon-carbon double bond is not attached directly to nitrogen,
  (j) alkynyl of three to twelve carbons,
    provided that a carbon of a carbon-carbon triple bond is not attached directly to nitrogen,
(10) —$C(X)NR_8R_9$,
(11) —$OSO_2R_{11}$ where $R_{11}$ is selected from
  (a) aryl,
  (b) cycloalkyl of three to twelve carbons,
  (c) alkyl of one to twelve carbons,
  (d) alkyl of one to twelve carbons substituted with 1, 2, 3, or 4 halo substituents, and
  (e) perfluoroalkyl of one to twelve carbons,
provided that when $R_A$ is (1)–(11), $L_1$ is a covalent bond,
(12) alkyl of one to twelve carbons,
(13) alkenyl of two to twelve carbons,
  provided that a carbon of a carbon-carbon double bond is not attached directly to $L_1$ when $L_1$ is other than a covalent bond,
(14) alkynyl of two to twelve carbons, provided that a carbon of a carbon-carbon triple bond is not attached directly to $L_1$ when $L_1$ is other than a covalent bond,
where (12), (13), and (14) can be optionally substituted with 1, 2, or 3 substituents independently selected from
  (a) alkoxy of one to twelve carbons,
  (b) —OH,
    provided that no two —OH groups are attached to the same carbon,
  (c) —SH,
    provided that no two —SH groups are attached to the same carbon,
  (d) —CN,
  (e) halo,
  (f) —CHO,
  (g) —$NO_2$,
  (h) haloalkoxy of one to twelve carbons,
  (i) perfluoroalkoxy of one to twelve carbons,
  (j) —$NR_7R_{7'}$,
  (k) =$NNR_7R_{7'}$,
  (l) —$NR_7NR_{7'}R_{7''}$ where $R_7$ and $R_{7'}$, are defined previously and $R_{7''}$ is selected from
    (i) hydrogen,
    (ii) aryl,
    (iii) cycloalkyl of three to twelve carbons,
    (vi) alkanoyl where the alkyl part is one to twelve carbons,
    (v) alkoxycarbonyl where the alkyl part is one to twelve carbons,
    (vi) alkoxycarbonyl where the alkyl part is one to twelve carbons substituted by 1 or 2 aryl groups,
    (vii) alkyl of one to twelve carbons,
    (viii) alkyl of one to twelve carbons substituted with 1 or 2 substituents independently selected from aryl or cycloalkyl of three to twelve carbons,
    (ix) alkenyl of three to twelve carbons,
      provided that a carbon-carbon double bond is not attached directly to nitrogen, and
    (x) alkynyl of three to twelve carbons,
      provided that a carbon-carbon triple bond is not attached directly to nitrogen,
  (m) —$CO_2R_{10}$ where $R_{10}$ is selected from
    (i) aryl,
    (ii) aryl substituted with 1, 2, or 3 alkyl of one to twelve carbon substituents,
    (ii) cycloalkyl of three to twelve carbons,
    (iii) alkyl of one to twelve carbons, and
    (iv) alkyl of one to twelve carbons substituted with aryl or cycloalkyl of three to twelve carbons,
  (n) —$C(X)NR_8R_9$,
  (o) =N—$OR_{10}$,
  (p) =$NR_{10}$,
  (q) —$S(O)_rR_{10}$, (r) —X'C(X)R$_{10}$,
(s) (=X), and
(t) —OSO$_2$R$_{11}$,

(15) cycloalkyl of three to twelve carbons,
(16) cycloalkenyl of four to twelve carbons,
provided that a carbon of a carbon-carbon double bond is not attached directly to L$_1$ when L$_1$ is other than a covalent bond,
where (15) and (16) can be optionally substituted with 1, 2, 3, or 4 substituents independently selected from
(a) alkyl of one to twelve carbons,
(b) aryl,
(c) alkoxy of one to twelve carbons,
(d) halo, and
(e) —OH,
provided that no two —OH groups are attached to the same carbon,
(17) perfluoroalkyl of one to twelve carbons,
(18) aryl, and
(19) heterocycle
where (18) and (19) can be optionally substituted with 1, 2, 3, 4, or 5 substituents independently selected from
(a) alkyl of one to twelve carbons,
(b) alkanoyloxy where the alkyl part is one to twelve carbons,
(c) alkoxycarbonyl where the alkyl part is one to twelve carbons,
(d) alkoxy of one to twelve carbons,
(e) halo,
(f) —OH,
provided that no two —OH groups are attached to the same carbon,
(g) thioalkoxy of one to twelve carbons,
(h) perfluoroalkyl of one to twelve carbons,
(i) —NR$_7$R$_{7'}$,
(j) —CO$_2$R$_{10}$,
(k) —OSO$_2$R$_{11}$, and
(l) (=X);

R$_1$, R$_2$, R$_3$, and R$_4$ are independently hydrogen or A; or R$_1$ and R$_2$ together are —X*—Y*—Z*— where X* is —O— or —CH$_2$—, Y* is —C(O)— or —(C(R$_{12}$)(R$_{13}$))$_v$— where R$_{12}$ and R$_{13}$ are independently hydrogen or alkyl of one to twelve carbons and v is 1, 2, or 3, and Z* is selected from —CH$_2$—, —CH$_2$S(O)$_t$—, —CH$_2$O—, —CH$_2$NR$_7$—, —NR$_7$—, and —O—;

L$_2$ is selected from
(1) a covalent bond,
(2) alkylene of one to twelve carbons,
(3) alkylene of one to twelve carbons substituted with 1 or 2 substituents independently selected from
(a) spiroalkyl of three to eight carbon atoms,
(b) spiroalkenyl of five or eight carbon atoms,
(c) oxo,
(d) halo, and
(e) —OH,
provided that no two —OH groups are attached to the same carbon,
(4) alkynylene of two to twelve carbons,
(5) —NR$_7$—,
(6) —C(X)—,
(7) —O—, and
(8) —S(O)$_t$—; and R$_5$ is selected from
(1) halo,
(2) —C(=NR$_7$)OR$_{10}$,
(3) —CN,
provided that when R$_5$ is (1), (2), or (3), L$_2$ is a covalent bond,
(4) alkyl of one to twelve carbons,
(5) alkynyl two to twelve carbons,
provided that a carbon of a carbon-carbon triple bond is not attached directly to L$_3$ when L$_3$ is other than a covalent bond,
(6) cycloalkyl of three to twelve carbons,
(7) heterocycle,
(8) aryl
where (4)–(8) can be optionally substituted with 1, 2, 3, 4, or 5 substituents independently selected from
(a) —OH,
provided that no two —OH groups are attached to the same carbon,
(b) —SH,
provided that no two —SH groups are attached to the same carbon,
(c) —CN,
(d) halo,
(e) —CHO,
(f) —NO$_2$,
(g) haloalkoxy of one to twelve carbons,
(h) perfluoroalkoxy of one to twelve carbons,
(i) —NR$_8$R$_{9'}$ where R$_8$ and R$_{9'}$ are selected from
(i) hydrogen,
(ii) alkanoyl where the alkyl part is one to twelve carbons,
(iii) alkoxycarbonyl where the alkyl part is one to twelve carbons,
(iv) alkoxycarbonyl where the alkyl part is one to twelve carbons and is substituted with 1 or 2 phenyl substituents,
(v) cycloalkyl of three to twelve carbons,
(vi) alkyl of one to twelve carbons,
(vii) alkyl of one to twelve carbons substituted with 1, 2, or 3 substituents independently selected from alkoxy of one to twelve carbons, cycloalkyl of three to twelve carbons, and aryl,
(viii) alkenyl of three to twelve carbons,
provided that a carbon of a carbon-carbon double bond is not directly attached to nitrogen,
(ix) alkynyl of three to twelve carbons,
provided that a carbon of a carbon-carbon triple bond is not directly attached to nitrogen,
(x) aryl,
(xi) aryl substituted with 1, 2, 3, 4, or 5 substituents independently selected from alkyl of one to twelve carbons,
alkanoyloxy where the alkyl part is one to twelve carbons,
alkoxycarbonyl where the alkyl part is one to twelve carbons,
alkoxy of one to twelve carbons,
halo,
—OH
provided that no two —OH groups are attached to the same carbon,
thioalkoxy of one to twelve carbons,
perfluoroalkyl of one to twelve carbons,
—NR$_7$R$_{7'}$,
—CO$_2$R$_{10}$,
—OSO$_2$R$_{11}$, and
(=X), or $R_{8'}$ and $R_{9'}$ together with the nitrogen atom to which they are attached form a ring selected from
(i) aziridine,
(ii) azetidine,
(iii) pyrrolidine,
(iv) piperidine,
(v) pyrazine,
(vi) morpholine,
(vii) thiomorpholine, and
(viii) thiomorpholine sulfone
where (i)–(viii) can be optionally substituted with 1, 2, or 3 alkyl of one to twelve carbon substituents,
(j) =$NNR_{8'}R_{9'}$,
(k) —$NR_7NR_{8'}R_{9'}$,
(l) —$CO_2R_8$,
(m) —$C(X)NR_{8'}R_{9'}$,
(n) =N—$OR_8$,
(o) =$NR_8$,
(p) —$S(O)_rR_{10}$,
(q) —X'C(X)$R_8$,
(r) (=X),
(s) —O—$(CH_2)_q$—Z—$R_{10}$ where $R_{10}$ is defined previously, q is 1, 2, or 3, and Z is O or —$S(O)_t$—,
(t) —$OC(X)NR_{8'}R_{9'}$,
(u) —$OSO_2R_{11}$,
(v) alkanoyloxy where the alkyl group is one to twelve carbons,
(w) —$L_BR_{30}$ where $L_B$ is selected from
(i) a covalent bond,
(ii) —O—,
(iii) —$S(O)_t$—, and
(iv) —C(X)— and
$R_{30}$ is selected from
(i) alkyl of one to twelve carbons,
(ii) alkenyl of one to twelve carbons,
provided that a carbon of a carbon-carbon double bond is not attached directly to $L_B$ when $L_B$ is other than a covalent bond,
(iii) alkynyl of one to twelve carbons,
provided that a carbon of a carbon-carbon triple bond is not attached directly to $L_B$ when $L_B$ is other than a covalent bond,
where (i), (ii), and (iii) can be optionally substituted with cycloalkyl of three to twelve carbons,
—OH,
provided that no two —OH groups are attached to the same carbon,
aryl, and
heterocycle,
(iv) aryl,
(v) aryl substituted with 1, 2, 3, 4, or 5 substituents independently selected from
alkyl of one to twelve carbons,
halo,
—$NO_2$, and
—OH,
provided that no two —OH groups are attached to the same carbon,
(vi) heterocycle, and
(vii) heterocycle substituted with 1, 2, 3, 4, or 5 substituents independently selected from
alkyl of one to twelve carbons,
halo,
—$NO_2$, and
—OH,
provided that no two —OH groups are attached to the same carbon, (x) —X'C(X)X''$R_{10}$,
(y) —C(=$NR_7$)$OR_{10}$, and
(z) —$NR_7(X)NR_{8'}R_{9'}$,

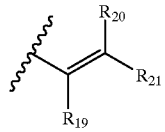

(9)
provided that when $R_5$ is (9), $L_3$ is other than —$NR_7$— or —O—,
where the carbon-carbon double bond is in the Z or E configuration, and
$R_{19}$, $R_{20}$, and $R_{21}$ are independently selected from
(a) hydrogen,
(b) halo,
(c) alkyl of one to twelve carbons, and
(d) alkyl of one to twelve carbons substituted with
(i) alkoxy of one to twelve carbons,
(ii) —OH,
provided that no two —OH groups are attached to the same carbon,
(iii) —SH,
provided that no two —SH groups are attached to the same carbon,
(iv) —CN,
(v) halo,
(vi) —CHO,
(vii) —$NO_2$,
(viii) haloalkoxy of one to twelve carbons,
(ix) perfluoroalkoxy of one to twelve carbons,
(x) —$NR_{8'}R_{9'}$,
(xi) =$NNR_{8'}R_{9'}$,
(xii) —$NR_7NR_{8'}R_{9'}$,
(xiii) —$CO_2R_{10}$,
(xiv) —$C(X)NR_{8'}R_{9'}$,
(xv) =N—$OR_{10}$,
(xvi) =$NR_{10}$,
(xvii) —$S(O)_rR_{10}$,
(xviii) —X'C(X)$R_{10}$,
(xix) (=X),
(xx) —O—$(CH_2)_q$—Z—$R_{10}$,
(xxi) —$OC(X)NR_{8'}R_{9'}$,
(xxii) —$L_BR_{30}$,
(xxiii) alkanoyloxy where the alkyl group is one to twelve carbons,
(xxiv) —$OSO_2R_{11}$, and
(xxv) —$NR_7(X)NR_{8'}R_{9'}$, or
$R_{20}$ and $R_{21}$ together are selected from
(a) cycloalkyl of three to twelve carbon atoms,
(b) cycloalkenyl of four to twelve carbon atoms, and
(c)

(c) (allene) where $R_{22}$ and $R_{23}$ are independently hydrogen or alkyl of one to twelve carbons, and
(10) cycloalkenyl of four to twelve carbons
where the cycloalkenyl group or the ring formed by $R_{20}$ and $R_{21}$ together can be optionally substituted with one or two substituents independently selected from
(a) alkoxy of one to twelve carbons,
(b) —OH,
provided that no two —OH groups are attached to the same carbon,
(c) —SH,
provided that no two —SH groups are attached to the same carbon,
(d) —CN,
(e) halo,
(f) —CHO,
(g) —NO$_2$,
(h) haloalkoxy of one to twelve carbons,
(i) perfluoroalkoxy of one to twelve carbons,
(j) —NR$_8$'R$_9$',
(k) =NNR$_8$'R$_9$',
(l) —NR$_7$NR$_8$'R$_9$',
(m) —CO$_2$R$_{10}$,
(n) —C(X)NR$_8$'R$_9$',
(o) =N—OR$_{10}$,
(p) =NR$_{10}$,
(q) —S(O)$_r$R$_{10}$,
(r) —X'C(X)R$_{10}$,
(s) (=X),
(t) —O—(CH$_2$)$_q$—Z—R$_{10}$,
(u) —OC(X)NR$_8$'R$_9$',
(v) —L$_B$R$_{30}$,
(w) alkanoyloxy where the alkyl group is one to twelve carbons,
(x) —OSO$_2$R$_{11}$, and
(y) —NR$_7$(X)NR$_8$'R$_9$';
R$_6$ is hydrogen or alkyl of one to twelve carbon atoms; or —L$_2$—R$_5$ and R$_6$ together are
(1)

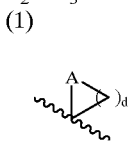

where d is 1, 2, 3, or 4 and A is selected from
(a) —CH$_2$—,
(b) —O—,
(c) —S(O)$_r$, and
(d) —NR$_7$—, or
(2)

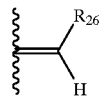

where the carbon-carbon double bond can be in the E or Z configuration and R$_{26}$ is selected from
(a) aryl,
(b) heterocycle,
(c) alkyl of one to twelve carbons,
(d) cycloalkyl of three to twelve carbons,
(e) cycloalkenyl of four to twelve carbons, and
(f) cycloalkenyl of four to twelve carbons where (a)–(f) can be optionally substituted with 1, 2, 3, 4, or 5 substituents independently selected from
(i) alkoxy of one to twelve carbons,
(ii) —OH,
provided that no two —OH groups are attached to the same carbon,
(iii) —SH,
provided that no two —SH groups are attached to the same carbon,
(iv) —CN,
(v) halo,
(vi) —CHO,
(vii) —NO$_2$,
(viii) haloalkoxy of one to twelve carbons,
(ix) perfluoroalkoxy of one to twelve carbons,
(x) —NR$_8$'R$_9$',
(xi) =NNR$_8$'R$_9$',
(xii) —NR$_7$NR$_8$'R$_9$',
(xiii) —CO$_2$R$_{10}$,
(xiv) —C(X)NR$_8$'R$_9$',
(xv) =N—OR$_{10}$,
(xvi) =NR$_{10}$,
(xvii) —S(O)$_r$R$_{10}$,
(xviii) —X'C(X)R$_{10}$,
(xix) (=X),
(xx) —O—(CH$_2$)$_q$—Z—R$_{10}$,
(xxi) —OC(X)NR$_8$'R$_9$',
(xxii) —L$_B$R$_{30}$,
(xxiii) alkanoyloxy where the alkyl group is one to twelve carbons,
(xxiii) —OSO$_2$R$_{11}$, and
(xxiv) —NR$_7$(X)NR$_8$'R$_9$'.

In another embodiment of the invention are disclosed methods of selectively partially antagonizing, antagonizing, agonizing or modulating the glucocorticoid receptor.

In another embodiment of the invention are disclosed methods of treating diseases comprising administering an effective amount of a compound having Formula I.

In yet another embodiment of the invention are disclosed pharmaceutical compositions containing compounds of Formula I.

Compounds of this invention include, but are not limited to,
2,5-dihydro-11-methoxy-5-phenyl-2,2,4-trimethyl-1H-[1]benzopyrano[3,4-f]quinoline,
2,5-dihydro-11-methoxy-5-(2-propenyl)-2,2,4-trimethyl-1H-[1]benzopyrano[3,4-f]quinoline,
2,5-dihydro-11-methoxy-5-(3,5-dichlorophenyl)-2,2,4-trimethyl-1H-[1]benzopyrano[3,4-f]quinoline, and
2,3,5-trihydro-11-methoxy-5-(3,5-dichlorophenyl)-2,2,4-dimethyl-4-methylene-1H-[1]benzopyrano[3,4-f]quinoline.

DETAILED DESCRIPTION OF THE INVENTION

Definition of Terms

The term "alkanoyl" refers to an alkyl group attached to the parent molecular group through a carbonyl group.

The term "alkanoyloxy" refers to an alkanoyl group attached to the parent molecular group through an oxygen atom.

The term "alkenyl" refers to a monovalent straight or branched chain group of two to twelve carbons derived from a hydrocarbon having at least one carbon-carbon double bond.

The term "alkoxy" refers to an alkyl group attached to the parent molecular group through an oxygen atom.

The term "alkoxycarbonyl" refers to an ester group, i.e. an alkoxy group attached to the parent molecular moiety through a carbonyl group.

The term "alkyl" refers to a monovalent straight or branched chain group of one to twelve carbons derived from a saturated hydrocarbon.

The term "alkylene" refers to a divalent straight or branched chain group of one to twelve carbons derived from an alkane.

The term "alkynyl" refers to a monovalent straight or branched chain hydrocarbon of two to twelve carbons with at least one carbon-carbon triple bond.

The term "alkynylene" refers to a divalent straight or branched chain group of two to twelve carbons derived from an alkyne.

The term "amino refers to —$NH_2$.

The term "aryl" refers to a mono- or bicyclic carbocyclic ring system having one or two aromatic rings. The aryl group can also be fused to a cyclohexane, cyclohexene, cyclopentane or cyclopentene ring.

The term "carboxy" refers to —$CO_2H$.

The term "cycloalkenyl" refers to a monovalent group derived from a cyclic or bicyclic hydrocarbon of three to twelve carbons that has at least one carbon-carbon double bond.

The term "cycloalkyl" refers to a monovalent group three to twelve carbons derived from a saturated cyclic or bicyclic hydrocarbon.

The term "halo" refers to F, Cl, Br, or I.

The term "heterocycle" represents a represents a 4-, 5-, 6- or 7-membered ring containing one, two or three heteroatoms independently selected from the group consisting of nitrogen, oxygen and sulfur. The 4- and 5-membered rings have zero to two double bonds and the 6- and 7-membered rings have zero to three double bonds. The term "heterocycle" also includes bicyclic, tricyclic and tetracyclic groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring. Heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolinyl, pyrrolyl, quinolinyl, quinoxaloyl, tetrahydrofuryl, tetrahydroisoquinolyl, tetrahydroquinolyl, tetrazolyl, thiadiazolyl, thiazolidinyl, thiazolyl, thienyl, thiomorpholinyl, triazolyl, and the like.

The term heterocycle also includes bridged bicyclic groups where a monocyclic heterocyclic group is bridged by an alkylene group such as

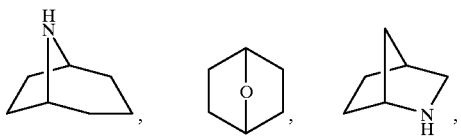

and the like.

The term heterocycle also include compounds of the formula

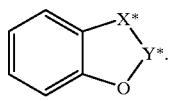

where X* is selected from —$CH_2$—, —$CH_2O$— and —O—, and Y* is selected from —C(O)— and —(C(R")$_2$)$_v$—, where R" is hydrogen or alkyl of one to four carbons, and v is 1–3. These heterocycles include 1,3-benzodioxolyl, 1,4-benzodioxanyl, and the like.

The term "N-protected amino" refers to groups intended to protect an amino group against undersirable reactions during synthetic procedures. Commonly used N-protecting groups are disclosed in Greene, "Protective Groups In Organic Synthesis," (John Wiley & Sons, New York (1981)). Preferred N-protecting groups are formyl, acetyl, benzoyl, pivaloyl, t-butylacetyl, phenylsulfonyl, benzyl, t-butyloxycarbonyl (Boc), and benzyloxycarbonyl (Cbz).

The term "O-protected carboxy" refers to a carboxylic acid protecting ester or amide group typically employed to block or protect the carboxylic acid functionality while the reactions involving other functional sites of the compound are performed. Carboxy protecting groups are disclosed in Greene, "Protective Groups in Organic Synthesis" (1981). Additionally, a carboxy protecting group can be used as a prodrug whereby the carboxy protecting group can be readily cleaved in vivo , for example by enzymatic hydrolysis, to release the biologically active parent. Such carboxy protecting groups are well known to those skilled in the art, having been extensively used in the protection of carboxyl groups in the penicillin and cephalosporin fields as described in U.S. Pat. Nos. 3,840,556 and 3,719,667.

The term "oxo" refers to (=O).

The term "pharmaceutically acceptable prodrugs" represents those prodrugs of the compounds of the present invention which are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug" represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The term "pharmaceutically acceptable salt" represents those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 1977, 66:1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Compounds of the present invention can exist as stereoisomers where asymmetric or chiral centers are present. These compounds are designated by the symbols "R" or "S," depending on the configuration of substituents around the chiral carbon atom. The present invention contemplates various stereoisomers and mixtures thereof. Stereoisomers include enantiomers and diastereomers, and equal mixtures of enantiomers are designated (±). Individual stereoisomers of compounds of the present invention can be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of enantiomers on chiral chromatographic columns.

Geometric isomers can also exist in the compounds of the present invention. The present invention contemplates the various geometric isomers and mixtures thereof resulting from the arrangement of substituents around a carbon-carbon double bond or arrangement of substituents around a ring. Substituents around a carbon-carbon double bond are designated as being in the Z or E configuration where the term "Z" represents substituents on the same side of the carbon-carbon double bond and the term "E" represents substituents on opposite sides of the carbon-carbon double bond. The arrangement of substituents around a ring are designated as cis or trans where the term "cis" represents substituents on the same side of the plane of the ring and the term "trans" represents substituents on opposite sides of the plane of the ring. Mixtures of compounds where the substituents are disposed on both the same and opposite sides of plane of the ring are designated cis/trans.

Methods for Radioligand Binding Studies with Human Glucocorticoid and Progesterone Receptor Cytosol The procedure described in Anal. Biochem. 1970, 37, 244–252, hereby incorporated by reference, was used. Briefly, cytosol preparations of human glucocorticoid receptor-α [GRX] isoform and human progesterone receptor-A [PRA] isoform were obtained from Ligand Pharmaceuticals (San Diego, Calif.). Both receptor cDNAs were cloned into baculovirus expression vectors and expressed in insect SF21 cells. [$^3$H]-dexamethasone (Dex, specific activity 82–86 Ci/mmole) and [$^3$H]-progesterone (Prog, specific activity 97–102 Ci/mmol) were purchased from Amersham Life Sciences (Arlington Heights, Ill.). Glass fiber type C multiscreen MAFC NOB plates were from Millipore (Burlington, Mass.). Hydroxyapatide Bio-Gel HTP gel was from Bio-Rad Laboratories (Hercules, Calif.). Tris (hydroxymethyl)aminomethane (Tris), ethylenediaminetetraacetic acid (EDTA), glycerol, dithiothreitol (DTT) and sodium moylybdate were obtained from Sigma Chemicals (St. Louis, Mo.). Microscint-20 scintillation fluid was from Packard Instrument (Meriden, Conn.).

Stock solutions (32 mM) of compounds were prepared in dimethylsulfoxide (DMSO), and 50× solutions of test compounds were prepared from the 32 mM solution with a 50:50 mixture of DMSO/ethanol. The 50× solution was then diluted with binding buffer that contained 10 mM Tri-HCl, 1.5 mM EDTA, 10% glycerol, 1 mM DTT, 20 mM sodium molybdate, pH 7.5 @ 4° C. 1% DMSO/ethanol was present in the binding assay.

GRX and PRA binding reactions were performed in Millipore Multiscreen plates. For GR binding assays, [$^3$H]-Dex (~35,000 dpm (~0.9 nM)), GRX cytosol (~35 μg protein), test compounds and binding buffer were mixed in a total volume of 200 μL and incubated at 4° C. overnight in a plate shaker. Specific binding was defined as the difference between binding of [$^3$H]Dex in the absence and in the presence of 1 μM unlabelled Dex.

For PR binding assays, [$^3$H]Prog (~36,000 dpm (~0.8 nM)), PRA cytosol (~40 μg protein), test compounds and binding buffer were mixed in a total volume of 200 μL and incubated at 4° C. at overnight in a plate shaker. Specific binding was defined as the difference between binding of [$^3$H]Prog in the absence and in the presence of 3 μM unlabelled Prog.

After an overnight incubation, 50 μL of hydroxyapatite (25% weight/volume) slurry were added to each well and plates were incubated for 10 min at ° C. in a plate shaker. Plates were suctioned with a Millipore vacuum manifold and each well was rinsed with 300 μL of ice-cold binding buffer. A 250 μL aliquot of Packard Microscint-20 was added to each well and the wells were shaken at room temperature for 20 minutes. The amount of radioactivity was determined with a Packard TopCount plate reader.

Determination of Inhibition Constant (Ki)

The concentration of test compounds that inhibited 50% of specific binding ($IC_{50}$) was determined from a Hill analysis of the competitive binding experiments. The Ki of test compounds was determined using the Cheng-Prusoff equation $Ki = IC_{50}/(1+[L^*]/[K_L])$ where $L^*$ is the concentration of radioligand and $K_L$ is the dissociation constant of the radioligand determined from saturation analysis. For GRX, $K_L$ was ~1.5 nM, and for PRA, $K_L$ was ~4.5 nM. The inhibitory potencies of compounds of this invention and their selectivity for GR and PR receptors are shown in Table 1.

TABLE 1

| Example Number | Ki (nM) | |
| --- | --- | --- |
| | GR | PR |
| 1 | 230 | 10000 |
| 2 | 640 | 14000 |
| 3 | 200 | 10000 |
| 4 | 270 | 8600 |

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants. Conversely, reduced particle size may maintain biological activity.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., *Methods in Cell Biology,* Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Abbreviations

Abbreviations that have been used in the descriptions of the scheme and the examples that follow are: $BF_3OEt_2$ for boron trifluoride diethyl etherate; DMF for N,N-dimethylformamide, DMSO for dimethylsulfoxide; and THF for tetrahydrofuran.

Synthetic Methods

The compounds and processes of the present invention will be better understood in connection with the following synthetic schemes which illustrate the methods by which the compounds of the invention can be prepared.

Syntheses of the compounds of the present invention are described in Schemes 1 and 2.

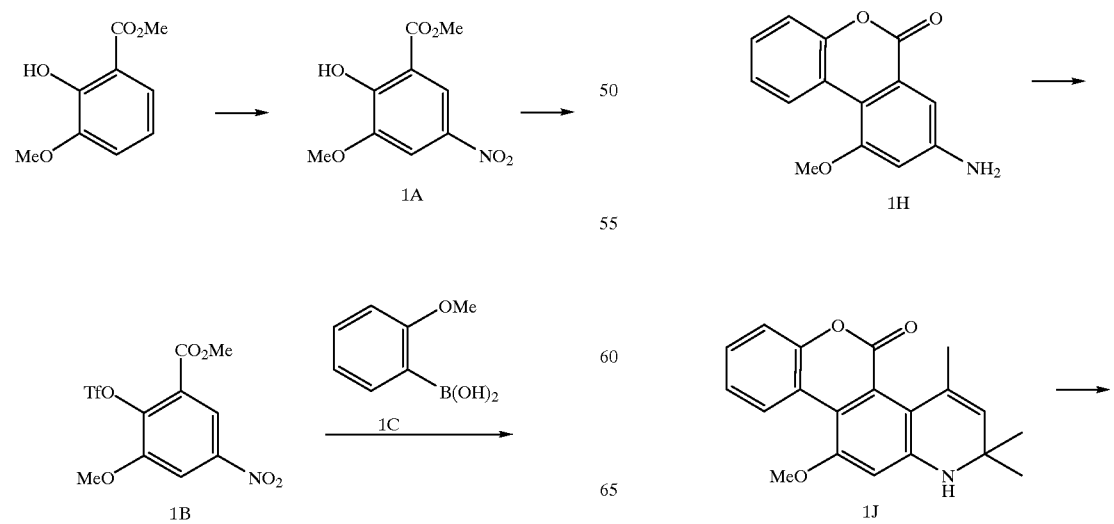

19

-continued

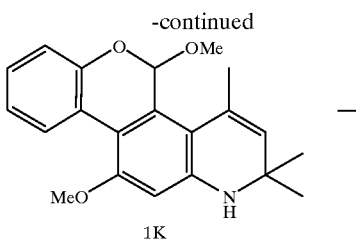

1K

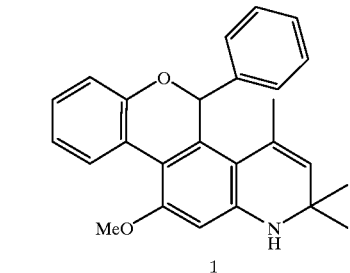

1

As shown in Scheme 1, methyl 2-hydroxy-3-methoxybenzoate (isovanillin) was nitrated with sodium nitrite in the presence of an acid such as trifluoroacetic acid to provide phenol 1A. 1A was then converted to the triflate 1B with reagents such as trifluoromethanesulfonic anhydride. Lithium/halogen exchange of substrates such as 2-bromoanisole with organolithium reagents such as n-butyllithium followed by treatment of the resulting anion with a trialkyl borate such as trimethyl- or triisopropylborate and hydrolysis with strong acid such as 2M HCl provided boronic acid 1C. Condensation of 1B with 1C in the presence of a palladium catalyst such as tetrakis(triphenylphosphine)palladium(0) or dichlorobis(triphenylphosphine)palladium(II) provided biphenyl 1D. Saponification 1D with a base such as lithium, sodium or potassium hydroxide provided carboxylic acid 1E. Conversion of 1E to lactone 1F was effected with Lewis acids such as BBr$_3$. Treatment of 1F with a non-nucleopholic base such as Cs$_2$CO$_3$ and alkylation of the resulting phenol with reagents such as dimethyl sulfate or methyl iodide produced alkyl-aryl ether 1G. Reduction of the nitro group in 1G with hydrogen gas and a palladium catalyst such as 10% palladium on carbon provided aniline 1H. Conversion of 1H to 1J was accomplished by a Skraup annulation reaction. 1J was converted to methyl acetal 1K by a two-step procedure consisting of conversion of 1J to its hemiacetal with reagents such as diisobutylaluminum hydride then acid-catalyzed etherification of the hemiacetal with acid such as p-toluenesulfonic acid monohydrate. 1J was also treated sequentially with Lewis acids such as BF$_3$.OEt$_2$ and organomagnesium chlorides, bromides, or iodides such as phenylmagnesium bromide to provide compounds exemplified by Example 1.

Scheme 2

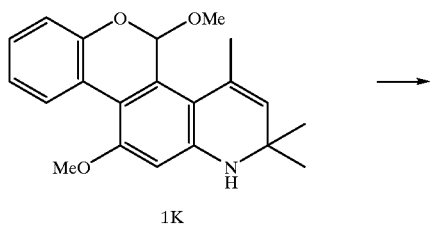

1K

20

-continued

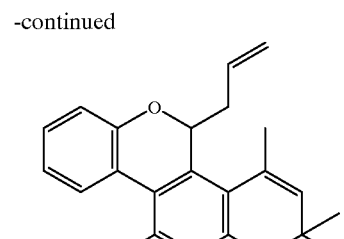

2

Acetal 1K was also treated with nucleophiles such as allyltrimethylsilane in the presence of Lewis acids such as boron trifluoride diethyl etherate to form compounds exemplified by Example 2.

The compounds and processes of the present invention will be better understood in connection with the following examples which are intended as an illustration of and not a limitation upon the scope of the invention as defined in the appended claims.

EXAMPLE 1

2,5-dihydro-11-methoxy-5-phenyl-2,2,4-trimethyl-1H-[1]benzopyrano[3,4-f]quinoline Example 1A A solution of methyl 2-hydroxy-3-methoxybenzoate (20.0 g, 110 mmol) in trifluoroacetic acid (150 mL) at 0° C. was treated with a solution of sodium nitrate (10.2 g, 121 mmol) in water (70 mL) over a period of 45 minutes, stirred at 0° C. for 30 minutes, and poured onto ice (450 mL). The precipitate was collected by filtration, washed with cold water, and dried under vacuum to provide the designated compound.

MS (DCI/NH$_3$) m/z 245 (M+NH$_4$)$^+$;

$^1$H NMR (300 MHz, CDCl$_3$) δ11.73 (s, 1H), 8.45 (d, J=7.8 Hz, 1H), 7.87 (d, J=8.2 Hz, 1H), 4.04 (s, 3H), 4.01 (s, 3H).

Example 1B

Example 1A (5.74 g, 25.3 mmol) in dichloromethane (100 mL) at −40° C. was treated with diisopropylethylamine (13.2 mL, 75.9 mmol) and freshly distilled triflic anhydride (10.0 g, 35.4 mmol) via addition funnel over a period of 30 minutes, stirred for 15 minutes at −40° C. when the starting phenol had been consumed, quenched with water (30 mL), stirred at 23° C. until a homogeneous, biphasic solution formed, and treated with dichloromethane (65 mL). The organic extract was washed with sequentially with 5% hydrochloric acid, brine, and saturated NaHCO$_3$, dried (Na$_2$SO$_4$), filtered, and concentrated. Recrystallization from hot hexanes provided the desired compound. The residue was purified by flash chromatography with 15% ethyl acetate/hexanes to provide the desired compound that can be stored indefinitely under nitrogen at −10° C. without detectable decomposition.

mp 84–86° C.

MS (DCI/NH$_3$) m/z 377 (M+NH$_4$)$^+$;

$^1$H NMR (300 MHz, CDCl$_3$) δ8.46 (d, J=7.8 Hz, 1H), 8.05 (d, J=7.7 Hz, 1H), 4.06 (s, 3H), 4.01 (s, 3H);

$^{13}$C NMR (75 MHz, CDCl$_3$) δ162.4, 152.6, 146.6, 141.4, 126.4, 120.6, 118.1, 111.1, 57.1, 53.2; Anal. calcd for $C_{10}H_8F_3NO_8S$: C, 33.43; H, 2.24; N, 3.89. Found: C, 33.69; H, 2.27; N, 3.81.

Example 1C

A solution of 2-bromoanisole (31.6 g, 169 mmol) in THF (320 mL) at −78° C. was treated with n-butyllithium (74.3 mL of a 2.5 M solution in hexanes, 186 mmol) for 30 minutes, stirred at −78° C. for 30 minutes, treated with triisopropylborate (48.7 mL, 211 mmol) in diethyl ether (20 mL) for 45 minutes, stirred for 30 minutes at −78° C., stirred at 23° C. for 2 hours, poured into a mixture of ice (150 mL), 3M HCl (150 mL), and ethyl acetate (600 mL), and stirred vigorously until a homogenous biphasic solution (pH 2) formed. The layers were separated, and the organic extract was dried ($Na_2SO_4$), filtered, concentrated, refiltered, and washed with hexanes (2×30 mL) to provide the desired compound. (Note: Slow addition of triisopropylborate is essential for the avoidance of side-products resulting from overaddition of the organolithium. The boronic acid was dried under vacuum briefly (30 minutes) then stored under nitrogen until use.)

MS (DCI/$NH_3$) m/z 170 (M+$NH_4$)$^+$;

$^1$H NMR (300 MHz, DMSO-$d_6$) δ7.67 (s, 2H), 7.57 (dd, J=7.3, 1.3 Hz, 1H), 7.87 (ddd, J=7.9, 7.4, 1.4 Hz, 1H), 6.98–6.91 (m, 2H), 3.81 (s, 3H).

Example 1D

A mechanically stirred mixture of Example 1B (7.22 g, 20.1 mmol), Example 1C (1.98 g, 13.1 mmol, 0.65 equiv), and potassium phosphate (8.53 g, 40.2 mmol) were treated sequentially with anhydrous dioxane (85 mL) and tetrakis(triphenylphosphine)palladium(0) catalyst (1.13 g, 1.00 mmol), heated at reflux for 18 hours, treated with two portions of Example 1C (1.98 g each) at 6 and 12 hour intervals, cooled to 23° C., and partitioned between ethyl acetate (300 mL) and water (100 mL). The organic layer was washed with 10% NaOH (50 mL) and brine (50 mL), dried ($Na_2SO_4$), filtered, and concentrated. The residue was purified by flash chromatography with 20% ethyl acetate/hexanes to provide the desired compound.

mp 137.5–140° C.;

MS (DCI/$NH_3$) m/z 335 (M+$NH_4$)$^+$ and 318 (M+H)$^+$;

$^1$H NMR (300 MHz, CDCl$_3$) δ8.36 (d, J=2.2 Hz, 1H), 7.93 (d, J=2.2 Hz, 1H), 7.39 (ddd, J=8.4, 7.5, 1.5 Hz, 1H), 7.12 (dd, J=7.5, 1.7 Hz, 1H), 7.04 (td, J=7.5, 1.6 Hz, 1H), 6.97 (d, J=8.5 Hz, 1H), 3.86 (s, 3H), 3.72 (s, 3H), 3.65 (s, 3H); Anal. calcd for $C_{16}H_{15}NO_6$: C, 60.56; H, 4.76; N, 4.41. Found: C, 60.64; H, 4.51; N, 4.39.

Example 1E

A solution of Example 1D (2.08 g, 6.55 mmol) in THF (10 mL) at 23° C. was treated with methanol (10 mL) and 20% KOH (10 mL), stirred at 23° C. for 6 hours, diluted with ethyl acetate (30 mL) and water (20 mL), and partitioned. The organic extract was extracted with water (10 mL) and the combined aqueous portions were cooled in ice water, acidified to pH 2 by dropwise treatment with 6M HCl, filtered, and washed in cold water (10 mL). The residue was dried under vacuum to provide the desired compound.

MS (DCI/$NH_3$) m/z 321 (M+$NH_4$)$^+$;

$^1$H NMR (300 MHz, DMSO-$d_6$) δ13.01 (br s, 1H), 8.12 (d, J=2.2 Hz, 1H), 7.96 (d, J=2.2 Hz, 1H), 7.33 (ddd, J=8.4, 7.6, 1.7 Hz, 1H), 7.08–7.02 (m, 2H), 6.97 (td, J=7.5, 1.2 Hz, 1H), 3.82 (s, 3H), 3.65 (s, 3H).

Example 1F

Example 1E (2.96 g, 9.75 mmol) in anhydrous dichloromethane (50 mL) at −78° C. was treated with boron tribromide (5.53 mL, 58.5 mmol, 6 equiv), warmed to 23° C. at which time all the boron tribromide went into solution to form a deep reddish-orange, homogenous solution, stirred at 23° C. for 12 hours, and then recooled to −78° C., and quenched by the addition of anhydrous methanol (15 mL). The cooling bath was removed after 2 hours of stirring at −78° C., and the reaction mixture was concentrated to remove trimethyl borate formed during the quench. The residue was treated with dichloromethane (30 mL) and methanol (3 mL), cooled to 0° C., and filtered to provide the desired compound. The filtrate was concentrated to provide a second crop of the desired compound.

mp>270° C.;

MS (DCI/$NH_3$) m/z 275 (M+$NH_4$)$^+$;

$^1$H NMR (300 MHz, DMSO-$d_6$) δ12.11 (s, 1H), 9.0 (d, J=8.2 Hz, 1H), 8.37 (d, J=2.2 Hz, 1H), 8.04 (d, J=2.2 Hz, 1H), 7.62 (t, J=7.6 Hz, 1H), 7.46–7.38 (m, 2H).

Example 1G

A solution of Example 1F (279 mg, 1.08 mmol) and anhydrous cesium carbonate (495 mg, 1.52 mmol) in dry DMF (5 mL) at 23° C. was treated dropwise with methyl iodide (95 mL, 1.5 mmol), stirred at 23° C. for 2.5 hours, diluted with water (3 mL) and 1:1 ethyl acetate/hexane (20 mL), and stirred for 15 minutes. The solids which formed at the interface of the biphasic mixture were filtered, washed with water (3 mL), and dried under vacuum to provide the desired compound.

mp 250–253° C.;

MS (DCI/$NH_3$) m/z 289 (M+$NH_4$)$^+$;

$^1$H NMR (300 MHz, CDCl$_3$) δ9.01 (dd, J=7.9, 1.4 Hz, 1H), 8.94 (d, J=2.0 Hz, 1H), 8.13 (d, J=2.1 Hz, 1H), 7.59 (ddd, J=7.9, 7.4, 1.6 Hz, 1H), 7.41 (dd, J=7.7, 1.6 Hz, 1H), 7.37 (ddd, J=7.7, 7.4, 1.4 Hz, 1H), 4.22 (s, 3H).

Example 1H

A solution of Example 1G (241 mg, 0.888 mmol) in dry dioxane (7 mL) at 23° C. was treated with 10% palladium on carbon (25 mg). A reflux condenser was attached to the reaction vessel with three-way adapter equipped with a hydrogen balloon. The solution was heated at 60° C. and subjected to three purge/fill cycles with hydrogen, hydrogenated at atmospheric pressure for 24 hours, filtered through Celite® while hot, and rinsed through with additional hot THF (2×20 mL). The filtrate was concentrated to provide the desired compound.

mp 230–235° C.;

MS (DCI/$NH_3$) m/z 259 (M+$NH_4$)$^+$, 242 (M+H)$^+$;

$^1$H NMR (300 MHz, DMSO-$d_6$) δ8.75 (dd, J=7.4, 1.9 Hz, 1H), 7.38–7.25 (m, 3H), 7.13 (d, J=2.3 Hz, 1H), 6.82 (d, J=2.3 Hz, 1H), 5.99 (br s, 2H), 3.98 (s, 3H).

Example 1J

A solution of Example 1H (202 mg, 0.837 mmol), acetone (HPLC grade, 30 mL), and iodine (70 mg, 0.276 mmol) were sealed in an ACE glass high pressure vessel (250 mL), placed in a preheated oil bath (105° C.), stirred for 10 hours at 105° C., cooled to 23° C., and concentrated. The resulting brown oil was purified by flash chromatography with 5%–10%–30% ethyl acetate/hexanes) to provide the desired compound.

mp 229–231° C.;

MS (DCI/$NH_3$) m/z 339 (M+$NH_4$)$^+$, 322 (M+H)$^+$;

$^1$H NMR (300 MHz, DMSO-$d_6$) δ8.76 (dd, J=8.1, 1.4 Hz, 1H), 7.35 (td, J=8, 0, 1.5 Hz, 1H), 7.30–7.22 (m, 2H), 6.95

(br s, 1H), 6.82 (s, 1H), 5.36 (br s, 2H), 3.97 (s, 3H), 1.90 (s, 3H), 1.22 (s, 6H);

HRMS (FAB/NBA) calcd for $C_{20}H_{20}NO_3$ $(M+H)^+$ 322.1443. Found: 322.1430; Anal. calcd for $C_{20}H_{19}NO_3$: C, 74.75; H, 5.96; N, 4.36. Found: C, 74.71; H,5.92; N, 4.40.

Example 1K

A solution of Example 1J (340 mg, 1.06 mmol) in anhydrous dichloromethane (10 mL) at −78° C. was treated dropwise with diisobutylaluminum hydride (2.22 mL of a 1.0 M solution in toluene, 2.22 mmol) for 20 minutes, stirred at −78° C. for 1 hour at which time TLC analysis of the reaction mixture (quenched with satd.$NH_4Cl$) indicated nearly complete conversion to the desired lactol and a small amount of diol resulting from over-reduction of the lactone. The solution was quenched with saturated sodium potassium tartrate (Rochelle's salt solution, 5 mL), warmed to room temperature, quenched with ethyl acetate (25 mL) and additional saturated sodium potassium tartrate (10 mL) and stirred vigorously until a homogeneous, biphasic solution resulted. The layers were separated and the aqueous layer was extracted with ethyl acetate (2×10 mL). The organic portions were combined, washed with brine (10 mL), and dried ($Na_2SO_4$), filtered and concentrated to provide the crude lactol.

The crude lactol was suspended in methanol (20 mL) at 0° C., treated with p-toluenesulfonic acid monohydrate (35 mg, 10% w/w), stirred for 1 hour, warmed to 10° C., poured into saturated $NaHCO_3$ (20 mL), and extracted with ethyl acetate (2×45 mL). The extracts were washed with brine (10 mL), ($Na_2SO_4$), filtered and concentrated. The residue was purified by flash chromatography with 30% hexanes/dichloromethane to provide the desired compound.

MS (DCI/$NH_3$) m/z 306 (M—$OCH_3)^+$;

$^1$H NMR (300 MHz, DMSO-$d_6$) δ8.18 (dd, J=8.0, 1.4 Hz, 1H), 7.16–6.96 (m, 3H), 6.47 (s, 1H), 6.33 (s, 1H), 5.38 (br s, 1H), 5.08 (s, 1H), 3.81 (s, 6H), 2.18 (s, 3H), 1.27 (s, 3H), 1.06 (s, 3H).

Example 1L 2,5-dihydro-11-methoxy-5-phenyl-2,2,4-trimethyl-1H-[1]benzopyrano[3,4-f]quinoline A solution of Example 1K (94 mg, 0.278 mmol) in dichloroethane (12 mL) at −10° C. was treated with freshly distilled $BF_3OEt_2$ (96 mL, 0.780 mmol), stirred at −10° C. for 5 minutes, treated dropwise with phenylmagnesium bromide (279 mL of a 3.0 M solution) in diethyl ether (0.834 mmol), stirred for 30 minutes at −10° C., poured into saturated $NaHCO_3$ (10 mL) and extracted with ethyl acetate (2×25 mL). The extract was washed with brine (5 mL), dried ($Na_2SO_4$), filtered, and concentrated. The residue was purified by flash chromatography with toluene to provide the desired compound.

MS (DCI/$NH_3$) m/z 384 $(M+H)^+$;

$^1$H NMR (300 MHz, DMSO-$d_6$) δ8.01 (dd, J=7.9, 1.3 Hz, 1H), 7.23–7.13 (m, 5H), 6.90 (td, J=7.7, 1.2 Hz, 1H), 6.83–6.72 (m, 2H), 6.78 (s, 1H), 6.48 (s, 1H), 6.34 (br s, 1H), 5.29 (s, 1H), 3.83 (s, 3H), 1.82 (s, 3H), 1.23 (s, 3H), 1.19 (s, 3H);

HRMS (FAB/NBA) calcd for $C_{26}H_{25}NO_2M^+$: 383.1885. Found: 383.1875.

EXAMPLE 2

2,5-dihydro-11-methoxy-5-(2-propenyl)-2,2,4-trimethyl-1H-[1]benzopyrano[3,4-f]quinoline A solution of Example 1K (102 mg, 0.302 mmol) and trimethylallylsilane (288 mL, 1.81 mmol) in dichloromethane (6 mL) at −78° C. was treated with freshly distilled $BF_3OEt_2$ (112 mL, 0.907 mmol), warmed to 23° C., stirred for 1.5 hours, poured into saturated $NaHCO_3$ (5 mL), and extracted with ethyl acetate (2×20 mL). The extract was washed with brine (3 mL), dried ($Na_2SO_4$), filtered, and concentrated. The residue was purified by flash chromatography with 100% toluene to provide the desired compound.

mp 84–86° C.;

MS (DCI/$NH_3$) m/z 348 $(M+H)^+$;

$^1$H NMR (300 MHz, DMSO-$d_6$) δ8.14 (dd, J=7.9, 1.3 Hz, 1H), 7.08 (td, J=7.8, 1.3 Hz, 1H), 6.95 (t, J=7.7 Hz, 1H), 6.84 (d, J=7.8 Hz, 1H), 6.37 (s, 1H), 6.28 (s, 1H), 5.88–5.73 (m, 2H), 5.35 (s, 1H), 5.06–4.94 (m, 2H), 3.81 (s, 3H), 2.47–2.31 (m, 2H), 2.13 (s, 3H), 1.21 (s, 3H), 1.13 (s, 3H); Anal. calcd for $C_{23}H_{25}NO$: C, 79.51; H, 7.25; N, 4.03. Found: C, 79.48; H, 7.18; N, 3.97.

EXAMPLE 3

2,5-dihydro-11-methoxy-5-(3,5-dichlorophenyl)-2,2,4-trimethyl-1H-[1]benzopyrano[3,4-f]quinoline A mixture of magnesium turnings (194 mg, 8.00 mmol) and 1-bromo-3,5-dichlorobenzene, (1.81 g, 8.00 mmol) diethyl ether (10 mL) was treated with a trace of iodine and stirred at gentle reflux for 2 hours at which point all of the magnesium had been consumed. The solution of Grignard reagent was stored under nitrogen and processed immediately with Example 1K as in Example 1L to provide the desired compound.

$^1$H NMR (300 MHz, DMSO-$d_6$) δ8.04 (dd, J=7.7, 1.2 Hz, 1H), 7.52–7.43 (m, 1H), 7.13 (dd, J=7.8, 1.3 Hz, 1H), 7.00–6.78 (m, 4H), 6.80 (s, 1H), 6.52 (s, 1H), 6.47 (br s, 1H), 5.32 (br s, 1H), 3.85 (s, 3H), 1.82 (s, 3H), 1.22 (s, 3H), 1.18 (s, 3H); HRMS (FAB/NBA) calcd for $C_{26}H_{23}Cl_2NO_2M^+$: 451.1106. Found: 451.1117.

EXAMPLE 4

2,3,5-trihydro-11-methoxy-5-(3,5-dichlorophenyl)-2,2,4-dimethyl-4-methylene-1H-[1]benzopyrano[3,4-f]quinoline Example 1K and 3,5-dichlorophenylmagnesium bromide were processed as in examples 1L and 3 to provide the title compound.

MS (DCI/$NH_3$) m/z 452 $(M+H)^+$;

$^1$H NMR (300 MHz, DMSO-$d_6$) δ8.04 (dd, J=7.7, 1.2 Hz, 1H), 7.50–7.42 (m, 1H), 7.19–7.13 (m, 2H), 7.01–6.77, m, 4H), 6.70 (br s, 1H), 6.52 (s, 1H), 6.39 (s, 1H), 4.79 (br s, 1H), 1.82 (s, 3H), 2.38–2.11 (m, 2H), 1.22 (s, 3H), 1.18 (s, 3H);

HRMS (FAB/NBA) calcd for $C_{26}H_{23}Cl_2NO_2.(M^+)$: 451.1106. Found: 451.1098.

What is claimed is:

1. A method of selectively modulating the activation, repression, agonism, and antagonism effects of the glucocorticoid receptor and not progesterone, androgen, estrogen, or mineralocorticoid receptors, in a mammal comprising administering an effective amount of a compound of the Formula;

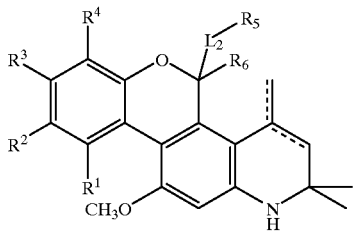

or pharmaceutically acceptable salts, and a pharmaceutical carrier, where the symbol—represents a single or double bond, provided that no two double bonds are in adjacent positions;

$R_1$, $R_2$, $R_3$, and $R_4$ are each independently hydrogen, or E; or $R_1$ and $R_2$ together are —X*—Y*—Z*— where X* is —O— or —$CH_2$—, Y* is —C(O)— or —$(C(R_{12})(R_{13}))_v$— where $R_{12}$ and $R_{13}$ are independently hydrogen or alkyl of one to twelve carbons and v is 1, 2, or 3, and Z* is selected from —$CH_2$—, —$CH_2S(O)_t$— where t is 0, 1, or 2,—$CH_2O$—, —$CH_2NR_7$—, —$NR_7$—, and —O—;

where E is —$L_E$—$R_E$ where $L_E$ is selected from
(1) a covalent bond,
(2) —O—,
(3) —$S(O)_t$— where t is 0, 1, or 2,
(4) —C(X)—, where X as used herein is selected from O or S,
(5) —$NR_7$— where $R_7$ is selected from
  (a) hydrogen,
  (b) aryl,
  (c) cycloalkyl of three to twelve carbons,
  (d) alkanoyl where the alkyl part is one to twelve carbons,
  (e) alkoxycarbonyl where the alkyl part is one to twelve carbons,
  (f) alkoxycarbonyl where the alkyl part is one to twelve carbons and is substituted by 1 or 2 aryl groups,
  (g) alkyl of one to twelve carbons,
  (h) alkyl of one to twelve carbons substituted with 1 or 2 substituents independently selected from aryl or cycloalkyl of three to twelve carbons,
  (i) alkenyl of three to twelve carbons, provided that a carbon of a carbon-carbon double bond is not attached directly to nitrogen,
  (j) alkynyl of three to twelve carbons, provided that a carbon of a carbon-carbon triple bond is not attached directly to nitrogen,
(6) —$NR_8C(X)NR_9$— where $R_8$ and $R_9$ are independently selected from
  (a) hydrogen,
  (b) aryl,
  (c) cycloalkyl of three to twelve carbons,
  (d) alkyl of one to twelve carbons,
  (e) alkyl of one to twelve carbons substituted with 1 or 2 substituents independently selected from aryl or cycloalkyl of three to twelve carbons,
  (f) alkenyl of three to twelve carbons, provided that a carbon of a carbon-carbon double bond is not attached directly to nitrogen,
  (g) alkynyl of three to twelve carbons, provided that a carbon of a carbon-carbon triple bond is not attached directly to nitrogen,
(7) —X'C(X)—, where X' as used herein is selected from O or S,
(8) —C(X)X'—,
(9) —X'C(X)X"—, where X" as used herein is selected from O or S, provided that when X is O, at least one of X' or X" is O,
(10) —$NR_8C(X)$—,
(11) —$C(X)NR_8$—,
(12) —$NR_8C(X)X'$—,
(13) —X'C(X)$NR_8$—,
(14) —$SO_2NR_8$—,
(15) —$NR_8SO_2$—, and
(16) —$NR_8SO_2N_9$— where (6)–(16) are drawn with their right ends attached to $R_E$ and, $R_E$ is selected from
(1) —OH,
(2) —OG where G is a —OH protecting group,
(3) —SH,
(4) —CN
(5) halo,
(6) haloalkoxy of one to twelve carbons,
(7) perfluoroalkoxy of one to twelve carbons,
(8) —CHO,
(9) —$NR_7R_7$, where $R_7$ is defined previously and, $R_7$, is selected from
  (a) hydrogen,
  (b) aryl,
  (c) cycloalkyl of three to twelve carbons,
  (d) alkanoyl where the alkyl part is one to twelve carbons,
  (e) alkoxycarbonyl where the alkyl part is one to twelve carbons,
  (f) alkoxycarbonyl where the alkyl part is one to twelve carbons and is substituted by 1 or 2 aryl groups,
  (g) alkyl of one to twelve carbons,
  (h) alkyl of one to twelve carbons substituted with 1 or 2 substituents independently selected from aryl or cycloalkyl of three to twelve carbons,
  (i) alkenyl of three to twelve carbons, provided that a carbon of a carbon-carbon double bond is not attached directly to nitrogen,
  (j) alkynyl of three to twelve carbons, provided that a carbon of a carbon-carbon triple bond is not attached directly to nitrogen,
(10) —$C(X)NR_8R_9$,
(11) —$OSO_2R_{11}$ where $R_{11}$ is selected from
  (a) aryl,
  (b) cycloalkyl of three to twelve carbons,
  (c) alkyl of one to twelve carbons,
  (d) alkyl of one to twelve carbons substituted with 1, 2, 3, or 4 halo substituents, and
  (e) perfluoroalkyl of one to twelve carbons, provided that when $R_E$ is (1)–(11), $L_E$ is a covalent bond,
(12) alkyl of one to twelve carbons,
(13) alkenyl of two to twelve carbons, provided that a carbon of a carbon-carbon double bond is not attached directly to $L_E$ when $L_E$ is other than a covalent bond,
(14) alkynyl of two to twelve carbons, provided that a carbon of a carbon-carbon triple bond is not attached directly to $L_E$ when $L_E$ is other than a covalent bond, where (12), (13), and (14) can be optionally substituted with 1, 2, or 3 substituents independently selected from
  (a) alkoxy of one to twelve carbons,
  (b) —OH, provided that no two —OH groups are attached to the same carbon,
  (c) —SH, provided that no two —SH groups are attached to the same carbon, (d) —CN,
(e) halo,
(f) —CHO,
(g) —NO$_2$,
(h) haloalkoxy of one to twelve carbons,
(i) perfluoroalkoxy of one to twelve carbons,
(j) —NR$_7$R$_7$,
(k) =NNR$_7$R$_7$,
(l) —NR$_7$NR$_7$R$_{7''}$ where R$_{7'}$ and R$_{7''}$ are defined previously and R$_{7''}$ is selected from
  (i) hydrogen,
  (ii) aryl,
  (iii) cycloalkyl of three to twelve carbons,
  (iv) alkanoyl where the alkyl part is one to twelve carbons,
  (v) alkoxycarbonyl where the alkyl part is one to twelve carbons,
  (vi) alkoxycarbonyl where the alkyl part is one to twelve carbons substituted by 1 or 2 aryl groups,
  (vii) alkyl of one to twelve carbons,
  (viii) alkyl of one to twelve carbons substituted with 1 or 2 substituents independently selected from aryl or cycloalkyl of three to twelve carbons,
  (ix) alkenyl of three to twelve carbons, provided that a carbon-carbon double bond is not attached directly to nitrogen, and
  (x) alkynyl of three to twelve carbons, provided that a carbon-carbon triple bond is not attached directly to nitrogen,
(m) —CO$_2$R$_{10}$ where R$_{10}$ is selected from
  (i) aryl,
  (ii) aryl substituted with 1, 2, or 3 alkyl of one to twelve carbon substituents,
  (iii) cycloalkyl of three to twelve carbons,
  (iv) alkyl of one to twelve carbons, and
  (v) alkyl of one to twelve carbons substituted with aryl or cycloalkyl of three to twelve carbons,
(n) —C(X)NR$_8$R$_9$,
(o) =N—OR$_{10}$,
(p) =NR$_{10}$,
(q) —S(O)$_t$R$_{10}$,
(r) —X'C(X)R$_{10}$,
(s) (=X), and
(t) —OSO$_2$R$_{11}$,
(15) cycloalkyl of three to twelve carbons,
(16) cycloalkenyl of four to twelve carbons,
provided that a carbon of a carbon-carbon double bond is not attached directly to L$_E$ when L$_E$ is other than a covalent bond, where (15) and (16) can be optionally substituted with 1, 2, 3, or 4 substituents independently selected from
  (a) alkyl of one to twelve carbons,
  (b) aryl,
  (c) alkoxy of one to twelve carbons,
  (d) halo, and
  (e) —OH,
  provided that no two —OH groups are attached to the same carbon,
(17) perfluoroalkyl of one to twelve carbons,
(18) aryl, and
(19) heterocycle
where (18) and (19) can be optionally substituted with 1, 2, 3, 4, or 5 substituents independently selected from
  (a) alkyl of one to twelve carbons,
  (b) alkanoyloxy where the alkyl part is one to twelve carbons,
  (c) alkoxycarbonyl where the alkyl part is one to twelve carbons,
  (d) alkoxy of one to twelve carbons,
  (e) halo,
  (f) —OH,
    provided that no two —OH groups are attached to the same carbon,
  (g) thioalkoxy of one to twelve carbons,
  (h) perfluoroalkyl of one to twelve carbons,
  (i) —NR$_7$R$_7$,
  (j) —CO$_2$R$_{10}$,
  (k) —OSO$_2$R$_{11}$, and
  (l) (=X);
L$_2$ is selected from
(1) a covalent bond,
(2) alkylene of one to twelve carbons,
(3) alkylene of two to twelve carbons substituted with 1 or 2 substituents independently selected from
  (a) spiroalkyl of three to eight carbon atoms,
  (b) spiroalkenyl of five or eight carbon atoms,
  (c) oxo,
  (d) halo, and
  (e) —OH,
  provided that no two —OH groups are attached to the same carbon,
(4) alkynylene of two to twelve carbons,
(5) —NR$_7$—,
(6) —C(X)—,
(7) —O—, and
(8) —S(O)$_t$—; and
R$_5$ is selected from
(1) halo,
(2) —C(=NR$_7$)OR$_{10}$,
(3) —CN,
provided that when R$_5$ is (1), (2), or (3), L$_2$ is a covalent bond,
(4) alkyl of one to twelve carbons,
(5) alkynyl of two to twelve carbons,
provided that a carbon of a carbon-carbon triple bond is not attached directly to L$_2$ when L$_2$ is other than a covalent bond,
(6) cycloalkyl of three to twelve carbons,
(7) heterocycle,
(8) aryl
where (4)–(8) can be optionally substituted with 1, 2, 3, 4, or 5 substituents independently selected from
  (a) —OH, provided that no two —OH groups are attached to the same carbon,
  (b) —SH, provided that no two —SH groups are attached to the same carbon,
  (c) —CN,
  (d) halo,
  (e) —CHO,
  (f) —NO$_2$,
  (g) haloalkoxy of one to twelve carbons,
  (h) perfluoroalkoxy of one to twelve carbons,
  (i) —NR$_8$R$_9$, where R$_{8'}$ and R$_{9'}$ are selected from
    (i) hydrogen,
    (ii) alkanoyl where the alkyl part is one to twelve carbons,
    (iii) alkoxycarbonyl where the alkyl part is one to twelve carbons,
    (iv) alkoxycarbonyl where the alkyl part is one to twelve carbons and is substituted with 1 or 2 phenyl substituents, (v) cycloalkyl of three to twelve carbons,
(vi) alkyl of one to twelve carbons,
(vii) alkyl of one to twelve carbons substituted with 1, 2, or 3 substituents independently selected from alkoxy of one to twelve carbons, cycloalkyl of three to twelve carbons, and aryl,
(viii) alkenyl of three to twelve carbons, provided that a carbon of a carbon-carbon double bond is not directly attached to nitrogen,
(ix) alkynyl of three to twelve carbons, provided that a carbon of a carbon-carbon triple bond is not directly attached to nitrogen,
(x) aryl,
(xi) aryl substituted with 1, 2, 3, 4, or 5 substituents independently selected from alkyl of one to twelve carbons, alkanoyloxy where the alkyl part is one to twelve carbons, alkoxycarbonyl where the alkyl part is one to twelve carbons, alkoxy of one to twelve carbons, halo, —OH provided that no two —OH groups are attached to the same carbon, thioalkoxy of one to twelve carbons, perfluoroalkyl of one to twelve carbons,
—$NR_7R_{7'}$,
—$CO_2R_{10}$,
—$OSO_2R_{11}$, and
(=X), or
$R_{8'}$ and $R_{9'}$ together with the nitrogen atom to which they are attached form a ring selected from
(i) aziridine,
(ii) azetidine,
(iii) pyrrolidine,
(iv) piperidine,
(v) pyrazine,
(vi) morpholine,
(vii) thiomorpholine, and
(viii) thiomorpholine sulfone
where (i)–(viii) can be optionally substituted with 1, 2, or 3 alkyl of one to twelve carbon substituents,
(j) =$NNR_8R_{9'}$,
(k) —$NR_7NR_8R_{9'}$,
(l) —$CO_2R_8$,
(m) —$C(X)NR_{8'}R_{9'}$,
(n) =N—$OR_8$,
(o) =$NR_8$,
(p) —$S(O)_tR_{10}$,
(q) —X'$C(X)R_8$,
(r) (=X),
(s) —O—$(CH_2)_q$—Z—$R_{10}$ where $R_{10}$ is defined previously, q is 1, 2, or 3, and Z is O or —$S(O)_t$—,
(t) —$OC(X)NR_8R_{9'}$,
(u) —$OSO_2R_{11}$,
(v) alkanoyloxy where the alkyl group is one to twelve carbons,
(w) —$L_BR_{30}$ where $L_B$ is selected from
(i) a covalent bond,
(ii) —O—,
(iii) —$S(O)_2$—, and
(iv) —C(X)— and
$R_{30}$ is selected from
(i) alkyl of one to twelve carbons,
(ii) alkenyl of two to twelve carbons, provided that a carbon of a carbon-carbon double bond is not attached directly to $L_B$ when $L_B$ is other than a covalent bond,
(iii) alkynyl of two to twelve carbons, provided that a carbon of a carbon-carbon triple bond is not attached directly to $L_B$ when $L_B$ is other than a covalent bond, where (i), (ii), and (iii) can be optionally substituted with cycloalkyl of three to twelve carbons, —OH, provided that no two —OH groups are attached to the same carbon, aryl, and heterocycle,
(iv) aryl,
(v) aryl substituted with 1, 2, 3, 4, or 5 substituents independently selected from alkyl of one to twelve carbons, halo, —$NO_2$, and —OH, provided that no two —OH groups are attached to the same carbon,
(vi) heterocycle, and
(vii) heterocycle substituted with 1, 2, 3, 4, or 5 substituents independently selected from alkyl of one to twelve carbons, halo, —$NO_2$, and —OH, provided that no two —OH groups are attached to the same carbon,
(x) —X'C(X)X"$R_{10}$,
(y) —C(=$NR_7$)$OR_{10}$, and
(z) —$NR_7(X)NR_8R_{9'}$,

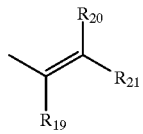

(9) provided that when $R_5$ is (9), $L_B$ is other than —$NR_7$— or —O—, where the carbon-carbon double bond is the Z or E configuration, and $R_{19}$, $R_{20}$, and $R_{21}$ are independently selected from
(a) hydrogen,
(b) halo,
(c) alkyl of one to twelve carbons, and
(d) alkyl of one to twelve carbons substituted with
(i) alkoxy of one to twelve carbons,
(ii) —OH, provided that no two —OH groups are attached to the same carbon,
(iii) —SH, provided that no two —SH groups are attached to the same carbon,
(iv) —CN,
(v) halo,
(vi) —CHO,
(vii) —$NO_2$,
(viii) haloalkoxy of one to twelve carbons,
(ix) perfluoroalkoxy of one to twelve carbons,
(x) —$NR_8R_{9'}$,
(xi) =$NNR_8R_{9'}$,
(xii) —$NR_7NR_8R_{9'}$,
(xiii) —$CO_2R_{10}$,
(xiv) —$C(X)NR_8R_{9'}$,
(xv) =N—$OR_{10}$,
(xvi) =$NR_{10}$,
(xvii) —$S(O)_tR_{10}$,
(xviii) —X'$C(X)R_{10}$,
(xix) (=X),
(xx) —O—$(CH_2)_q$—Z—$R_{10}$,
(xxi) —$OC(X)NR_8R_{9'}$,
(xxii) —$L_BR_{30}$,
(xxiii) alkanoyloxy where the alkyl group is one to twelve carbons,
(xxiv) —$OSO_2R_{11}$, and
(xxv) —$NR_7(X)NR_8R_{9'}$ or
$R_{20}$ and $R_{21}$ together are selected from
(a) cycloalkyl of three to twelve carbon atoms,
(b) cycloalkenyl of four to twelve carbon atoms, and (c)

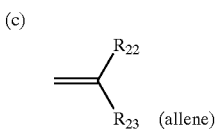

where $R_{22}$ and $R_{23}$ are independently hydrogen or alkyl of one to twelve carbons, and,

(10) cycloalkenyl of four to twelve carbons where the cycloalkenyl group or the ring formed by $R_{20}$ and $R_{21}$ together can be optionally substituted with one or two substituents independently selected from
(a) alkoxy of one to twelve carbons,
(b) —OH, provided that no two —OH groups are attached to the same carbon,
(c) —SH, provided that no two —SH groups are attached to the same carbon,
(d) —CN,
(e) halo,
(f) —CHO,
(g) —NO$_2$,
(h) haloalkoxy of one to twelve carbons,
(i) perfluoroalkoxy of one to twelve carbons,
(j) —NR$_8$·R$_9$·,
(k) =NNR$_8$·R$_9$·,
(l) —NR$_7$NR$_8$·R$_9$·,
(m) —CO$_2$R$_{10}$,
(n) —C(X)NR$_8$·R$_9$·,
(o) =N—OR$_{10}$,
(p) =NR$_{10}$,
(q) —S(O)$_r$R$_{10}$,
(r) —X'C(X)R$_{10}$,
(s) (=X),
(t) —O—(CH$_2$)$_q$—Z—R$_{10}$,
(u) —OC(X)NR$_8$·R$_9$·,
(v) —L$_B$R$_{30}$,
(w) alkanoyloxy where the alkyl group is one to twelve carbons,
(x) —OSO$_2$R$_{11}$, and
(y) —NR$_7$(X)NR$_8$·R$_9$·, $R_6$ is hydrogen or alkyl of one to twelve carbon atoms; or —L$_2$—R$_5$ and R$_6$ together are (1)

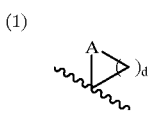

where d is 1, 2, 3, or 4 and A is selected from
(a) —CH$_2$—,
(b) —O—,
(c) —S(O)$_t$, and
(d) —NR$_7$—, or (2)

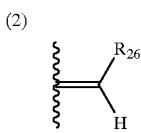

where the carbon-carbon double bond can be in the E or Z configuration and $R_{26}$ is selected from
(a) aryl,
(b) heterocycle,
(c) alkyl of one to twelve carbons,
(d) cycloalkyl of three to twelve carbons,
(e) cycloalkenyl of four to twelve carbons, and
(f) cycloalkenyl of four to twelve carbons where (a)–(f) can be optionally substituted with 1, 2, 3, 4, or 5 substituents independently selected from
(i) alkoxy of one to twelve carbons,
(ii) —OH, provided that no two —OH groups are attached to the sane carbon,
(iii) —SH, provided that no two —SH groups are attached to the same carbon,
(iv) —CN,
(v) halo,
(vi) —CHO,
(vii) —NO$_2$,
(viii) haloalkoxy of one to twelve carbons,
(ix) perfluoroalkoxy of one to twelve carbons,
(x) —NR$_8$·R$_9$·,
(xi) =NNR$_8$·R$_9$·,
(xii) —NR$_7$NR$_8$·R$_9$·,
(xiii) —CO$_2$R$_{10}$,
(xiv) —C(X)NR$_8$·R$_9$·,
(xv) =N—OR$_{10}$,
(xvi) =NR$_{10}$,
(xvii) —S(O)$_r$R$_{10}$,
(xviii) —X'C(X)R$_{10}$,
(xix) (=X),
(xx) —O—(CH$_2$)$_q$—Z—R$_{10}$,
(xxi) —OC(X)NR$_8$·R$_9$·,
(xxii) —L$_B$R$_{30}$,
(xxiii) alkanoyloxy where the alkyl group is one to twelve carbons,
(xxiv) —OSO$_2$R$_{11}$, and
(xxv) —NR$_7$(X)NR$_8$·R$_9$·.

2. A method of treating inflammation and immune, autoimmune and inflammatory diseases in a mammal comprising administering an effective amount of a compound having Formula:

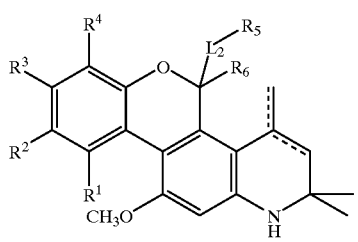

or pharmaceutically acceptable salts, where the symbol— represents a single or double bond, provided that no two double bonds are in adjacent positions;

$R_1$, $R_2$, $R_3$, and $R_4$ are each independently hydrogen, or E; or $R_1$ and $R_2$ together are —X*—Y*—Z*— where X* is —O— or —CH$_2$—, Y* is —C(O)— or —(C(R$_{12}$)(R$_{13}$))$_v$— where $R_{12}$ and $R_{13}$ are independently hydrogen or alkyl of one to twelve carbons and v is 1, 2, or 3, and Z* is selected from —CH$_2$—, —CH$_2$S(O)$_t$— where t is 0, 1, or 2, —CH$_2$O—, —CH$_2$NR$_7$—, —NR$_7$—, and —O—;

E is —L$_E$—R$_E$ where L$_E$ is selected from
(1) a covalent bond,
(2) —O—,
(3) —S(O)$_t$— where t is 0, 1, or 2,
(4) —C(X)—, where X as used herein is selected from O or S, (5) —NR$_7$— where R$_7$ is selected from
  (a) hydrogen,
  (b) aryl,
  (c) cycloalkyl of three to twelve carbons,
  (d) alkanoyl where the alkyl part is one to twelve carbons,
  (e) alkoxycarbonyl where the alkyl part is one to twelve carbons,
  (f) alkoxycarbonyl where the alkyl part is one to twelve carbons and is substituted by 1 or 2 aryl groups,
  (g) alkyl of one to twelve carbons,
  (h) alkyl of one to twelve carbons substituted with 1 or 2 substituents independently selected from aryl or cycloalkyl of three to twelve carbons,
  (i) alkenyl of three to twelve carbons, provided that a carbon of a carbon-carbon double bond is not attached directly to nitrogen,
  (j) alkynyl of three to twelve carbons, provided that a carbon of a carbon-carbon triple bond is not attached directly to nitrogen,
(6) —NR$_8$C(X)NR$_9$— where R$_8$ and R$_9$ are independently selected from
  (a) hydrogen,
  (b) aryl,
  (c) cycloalkyl of three to twelve carbons,
  (d) alkyl of one to twelve carbons,
  (e) alkyl of one to twelve carbons substituted with 1 or 2 substituents independently selected from aryl or cycloalkyl of three to twelve carbons,
  (f) alkenyl of three to twelve carbons, provided that a carbon of a carbon-carbon double bond is not attached directly to nitrogen,
  (g) alkynyl of three to twelve carbons, provided that a carbon of a carbon-carbon triple bond is not attached directly to nitrogen,
(7) —X'C(X)—, where X' as used herein is selected from O or S,
(8) —C(X)X'—,
(9) —X'C(X)X"—, where X" as used herein is selected from O or S, provided that when X is O, at least one of X' or X" is O,
(10) —NR$_8$C(X)—,
(11) —C(X)NR$_8$—,
(12) —NR$_8$C(X)X'—,
(13) —X'C(X)NR$_8$—,
(14) —SO$_2$NR$_8$—,
(15) —NR$_8$SO$_2$—, and
(16) —NR$_8$SO$_2$NR$_9$—
where (6)–(16) are drawn with their right ends attached to R$_E$ and, R$_E$ is selected from
(1) —OH,
(2) —OG where G is a —OH protecting group,
(3) —SH,
(4) —CN
(5) halo,
(6) haloalkoxy of one to twelve carbons,
(7) perfluoroalkoxy of one to twelve carbons,
(8) —CHO,
(9) —NR$_7$R$_7$, where R$_7$ is defined previously and, R$_7$, is selected from
  (a) hydrogen,
  (b) aryl,
  (c) cycloalkyl of three to twelve carbons,
  (d) alkanoyl where the alkyl part is one to twelve carbons,
  (e) alkoxycarbonyl where the alkyl part is one to twelve carbons,
  (f) alkoxycarbonyl where the alkyl part is one to twelve carbons and is substituted by 1 or 2 aryl groups,
  (g) alkyl of one to twelve carbons,
  (h) alkyl of one to twelve carbons substituted with 1 or 2 substituents independently selected from aryl or cycloalkyl of three to twelve carbons,
  (i) alkenyl of three to twelve carbons, provided that a carbon of a carbon-carbon double bond is not attached directly to nitrogen,
  (j) alkynyl of three to twelve carbons, provided that a carbon of a carbon-carbon triple bond is not attached directly to nitrogen,
(10) —C(X)NR$_8$R,
(11) —OSO$_2$R$_{11}$ where R$_{11}$ is selected from
  (a) aryl,
  (b) cycloalkyl of three to twelve carbons,
  (c) alkyl of one to twelve carbons,
  (d) alkyl of one to twelve carbons substituted with 1, 2, 3, or 4 halo substituents, and
  (e) perfluoroalkyl of one to twelve carbons, provided that when R$_E$ is (1)–(11), L$_E$ is a covalent bond,
(12) alkyl of one to twelve carbons,
(13) alkenyl of two to twelve carbons, provided that a carbon of a carbon-carbon double bond is not attached directly to L$_E$ when L$_E$ is other than a covalent bond,
(14) alkynyl of two to twelve carbons, provided that a carbon of a carbon-carbon triple bond is not attached directly to L$_E$ when L$_E$ is other than a covalent bond, where (12), (13), and (14) can be optionally substituted with 1, 2, or 3 substituents independently selected from
  (a) alkoxy of one to twelve carbons,
  (b) —OH, provided that no two —OH groups are attached to the same carbon,
  (c) —SH, provided that no two —SH groups are attached to the same carbon,
  (d) —CN,
  (e) halo,
  (f) —CHO,
  (g) —NO$_2$,
  (h) haloalkoxy of one to twelve carbons,
  (i) perfluoroalkoxy of one to twelve carbons,
  (j) —NR$_7$R$_7$,
  (k) =NNR$_7$R$_7$,
  (l) —NR$_7$NR$_7$R$_{7"}$ where R$_7$ and R$_{7'}$ are defined previously and R$_{7"}$ is selected from
    (i) hydrogen,
    (ii) aryl,
    (iii) cycloalkyl of three to twelve carbons,
    (iv) alkanoyl where the alkyl part is one to twelve carbons,
    (v) alkoxycarbonyl where the alkyl part is one to twelve carbons,
    (vi) alkoxycarbonyl where the alkyl part is one to twelve carbons substituted by 1 or 2 aryl groups,
    (vii) alkyl of one to twelve carbons,
    (viii) alkyl of one to twelve carbons substituted with 1 or 2 substituents independently selected from aryl or cycloalkyl of three to twelve carbons,
    (ix) alkenyl of three to twelve carbons, provided that a carbon-carbon double bond is not attached directly to nitrogen, and
    (x) alkynyl of three to twelve carbons, provided that a carbon-carbon triple bond is not attached directly to nitrogen, (m) —CO$_2$R$_{10}$ where R$_{10}$ is selected from
  (i) aryl,
  (ii) aryl substituted with 1, 2, or 3 alkyl of one to twelve carbon substituents,
  (iii) cycloalkyl of three to twelve carbons,
  (iv) alkyl of one to twelve carbons, and
  (v) alkyl of one to twelve carbons substituted with aryl or cycloalkyl of three to twelve carbons,
(n) —C(X)NR$_8$R$_9$,
(o) =N—OR$_{10}$,
(p) =NR$_{10}$,
(q) —S(O)$_t$R$_{10}$,
(r) —X'C(X)R$_{10}$,
(s) (=X), and
(t) —OSO$_2$R$_{11}$,

(15) cycloalkyl of three to twelve carbons,
(16) cycloalkenyl of four to twelve carbons,
provided that a carbon of a carbon-carbon double bond is not attached directly to L$_E$ when L$_E$ is other than a covalent bond, where (15) and (16) can be optionally substituted with 1, 2, 3, or 4 substituents independently selected from
  (a) alkyl of one to twelve carbons,
  (b) aryl,
  (c) alkoxy of one to twelve carbons,
  (d) halo, and
  (e) —OH,
  provided that no two —OH groups are attached to the same carbon,
(17) perfluoroalkyl of one to twelve carbons,
(18) aryl, and
(19) heterocycle
where (18) and (19) can be optionally substituted with 1, 2, 3, 4, or 5 substituents independently selected from
  (a) alkyl of one to twelve carbons,
  (b) alkanoyloxy where the alkyl part is one to twelve carbons,
  (c) alkoxycarbonyl where the alkyl part is one to twelve carbons,
  (d) alkoxy of one to twelve carbons,
  (e) halo,
  (f) —OH,
  provided that no two —OH groups are attached to the same carbon,
  (g) thioalkoxy of one to twelve carbons,
  (h) perfluoroalkyl of one to twelve carbons,
  (i) —NR$_7$R$_7$,
  (j) —CO$_2$R$_{10}$,
  (k) —OSO$_2$R$_{11}$, and
  (l) (=X);

L$_2$ is selected from
  (1) a covalent bond,
  (2) alkylene of one to twelve carbons,
  (3) alkylene of two to twelve carbons substituted with 1 or 2 substituents independently selected from
    (a) spiroalkyl of three to eight carbon atoms,
    (b) spiroalkenyl of five or eight carbon atoms,
    (c) oxo,
    (d) halo, and
    (e) —OH,
    provided that no two —OH groups are attached to the same carbon,
  (4) alkynylene of two to twelve carbons,
  (5) —NR$_7$—,
  (6) —C(X)—,
  (7) —O—, and
  (8) —S(O)$_t$—; and R$_5$ is selected from
  (1) halo,
  (2) —C(=NR$_7$)OR$_{10}$,
  (3) —CN,
  provided that when R$_5$ is (1), (2), or (3), L$_2$ is a covalent bond,
  (4) alkyl of one to twelve carbons,
  (5) alkynyl two to twelve carbons,
  provided that a carbon of a carbon-carbon triple bond is not attached directly to L$_2$ when L$_2$ is other than a covalent bond,
  (6) cycloalkyl of three to twelve carbons,
  (7) heterocycle,
  (8) aryl
  where (4)–(8) can be optionally substituted with 1, 2, 3, 4, or 5 substituents independently selected from
    (a) —OH, provided that no two —OH groups are attached to the same carbon,
    (b) —SH, provided that no two —SH groups are attached to the same carbon,
    (c) —CN,
    (d) halo,
    (e) —CHO,
    (f) —NO$_2$,
    (g) haloalkoxy of one to twelve carbons,
    (h) perfluoroalkoxy of one to twelve carbons,
    (i) —NR$_8$'R$_9$', where R$_8$' and R$_9$' are selected from
      (i) hydrogen,
      (ii) alkanoyl where the alkyl part is one to twelve carbons,
      (iii) alkoxycarbonyl where the alkyl part is one to twelve carbons,
      (iv) alkoxycarbonyl where the alkyl part is one to twelve carbons and is substituted with 1 or 2 phenyl substituents,
      (v) cycloalkyl of three to twelve carbons,
      (vi) alkyl of one to twelve carbons,
      (vii) alkyl of one to twelve carbons substituted with 1, 2, or 3 substituents independently selected from alkoxy of one to twelve carbons, cycloalkyl of three to twelve carbons, and aryl,
      (viii) alkenyl of three to twelve carbons, provided that a carbon of a carbon-carbon double bond is not directly attached to nitrogen,
      (ix) alkynyl of three to twelve carbons, provided that a carbon of a carbon-carbon triple bond is not directly attached to nitrogen,
      (x) aryl,
      (xi) aryl substituted with 1, 2, 3, 4, or 5 substituents independently selected from alkyl of one to twelve carbons, alkanoyloxy where the alkyl part is one to twelve carbons, alkoxycarbonyl where the alkyl part is one to twelve carbons, alkoxy of one to twelve carbons, halo, —OH provided that no two —OH groups are attached to the same carbon, thioalkoxy of one to twelve carbons, perfluoroalkyl of one to twelve carbons,
      —NR$_7$R$_7$,
      —CO$_2$R$_{10}$,
      —OSO$_2$R$_{11}$, and
      (=X), or $R_{8'}$ and $R_{9'}$ together with the nitrogen atom to which they are attached form a ring selected from
(i) aziridine,
(ii) azetidine,
(iii) pyrrolidine,
(iv) piperidine,
(v) pyrazine,
(vi) morpholine,
(vii) thiomorpholine, and
(viii) thiomorpholine sulfone
where (i)–(viii) can be optionally substituted with 1, 2, or 3 alkyl of one to twelve carbon substituents,
(j) $=NNR_{8'}R_{9'}$,
(k) $-NR_7NR_{8'}R_{9'}$,
(l) $-CO_2R_8$,
(m) $-C(X)NR_{8'}R_{9'}$,
(n) $=N-OR_8$,
(o) $=NR_8$,
(p) $-S(O)_rR_{10}$,
(q) $-X'C(X)R_8$,
(r) $(=X)$,
(s) $-O-(CH_2)_q-Z-R_{10}$ where $R_{10}$ is defined previously, q is 1, 2, or 3, and Z is O or $-S(O)_r-$,
(t) $-OC(X)NR_{8'}R_{9'}$,
(u) $-OSO_2R_{11}$,
(v) alkanoyloxy where the alkyl group is one to twelve carbons,
(w) $-L_BR_{30}$ where $L_B$ is selected from
(i) a covalent bond,
(ii) $-O-$,
(iii) $-S(O)_2-$, and
(iv) $-C(X)-$ and
$R_{30}$ is selected from
(i) alkyl of one to twelve carbons,
(ii) alkenyl of two to twelve carbons, provided that a carbon of a carbon-carbon double bond is not attached directly to $L_B$ when $L_B$ is other than a covalent bond,
(iii) alkynyl of two to twelve carbons, provided that a carbon of a carbon-carbon triple bond is not attached directly to $L_B$ when $L_B$ is other than a covalent bond,
where (i), (ii), and (iii) can be optionally substituted with cycloalkyl of three to twelve carbons, $-OH$, provided that no two $-OH$ groups are attached to the same carbon, aryl, and heterocycle,
(iv) aryl,
(v) aryl substituted with 1, 2, 3, 4, or 5 substituents independently selected from alkyl of one to twelve carbons, halo, $-NO_2$, and $-OH$, provided that no two $-OH$ groups are attached to the same carbon,
(vi) heterocycle, and
(vii) heterocycle substituted with 1, 2, 3, 4, or 5 substituents independently selected from alkyl of one to twelve carbons, halo, $-NO_2$, and $-OH$, provided that no two $-OH$ groups are attached to the same carbon, (x) $-X'C(X)X''R_{10}$,
(y) $-C(=NR_7)OR_{10}$, and
(z) $-NR_7(X)NR_{8'}R_{9'}$,

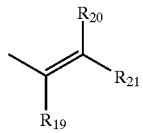

(9)
provided that when $R_5$ is (9), $L_B$ is other than $-NR_7-$ or $-O-$, where the carbon-carbon double bond is the Z or E configuration, and $R_{19}$, $R_{20}$, and $R_{21}$ are independently selected from
(a) hydrogen,
(b) halo,
(c) alkyl of one to twelve carbons, and
(d) alkyl of one to twelve carbons substituted with
(i) alkoxy of one to twelve carbons,
(ii) $-OH$, provided that no two $-OH$ groups are attached to the same carbon,
(iii) $-SH$, provided that no two $-SH$ groups are attached to the same carbon,
(iv) $-CN$,
(v) halo,
(vi) $-CHO$,
(vii) $-NO_2$,
(viii) haloalkoxy of one to twelve carbons,
(ix) perfluoroalkoxy of one to twelve carbons,
(x) $-NR_{8'}R_{9'}$,
(xi) $=NNR_{8'}R_{9'}$,
(xii) $-NR_7NR_{8'}R_{9'}$,
(xiii) $-CO_2R_{10}$,
(xiv) $-C(X)NR_{8'}R_{9'}$,
(xv) $=N-OR_{10}$,
(xvi) $=NR_{10}$,
(xvii) $-S(O)_rR_{10}$,
(xviii) $-X'C(X)R_{10}$,
(xix) $(=X)$,
(xx) $-O-(CH_2)_q-Z-R_{10}$,
(xxi) $-OC(X)NR_{8'}R_{9'}$,
(xxii) $-L_BR_{30}$,
(xxiii) alkanoyloxy where the alkyl group is one to twelve carbons,
(xxiv) $-OSO_2R_{11}$, and
(xxv) $-NR_7(X)NR_{8'}R_{9'}$, or
$R_{20}$ and $R_{21}$ together are selected from
(a) cycloalkyl of three to twelve carbon atoms,
(b) cycloalkenyl of four to twelve carbon atoms, and (c)
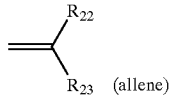
(allene)

where $R_{22}$ and $R_{23}$ are independently hydrogen or alkyl of one to twelve carbons, and
(10) cycloalkenyl of four to twelve carbons where the cycloalkenyl group or the ring formed by $R_{20}$ and $R_{21}$ together can be optionally substituted with one or two substituents independently selected from
(a) alkoxy of one to twelve carbons,
(b) $-OH$, provided that no two $-OH$ groups are attached to the same carbon, (c) —SH, provided that no two —SH groups are attached to the same carbon,
(d) —CN,
(e) halo,
(f) —CHO,
(g) —NO$_2$,
(h) haloalkoxy of one to twelve carbons,
(i) perfluoroalkoxy of one to twelve carbons,
(j) —NR$_8$·R$_9$·,
(k) =NNR$_8$·R$_9$·,
(l) —NR$_7$NR$_8$·R$_9$·,
(m) —CO$_2$R$_{10}$,
(n) —C(X)NR$_8$·R$_9$·,
(o) =N—OR$_{10}$,
(p) =NR$_{10}$,
(q) —S(O)$_r$R$_{10}$,
(r) —X'C(X)R$_{10}$,
(s) (=X),
(t) —O—(CH$_2$)$_q$—Z—R$_{10}$,
(u) —OC(X)NR$_8$·R$_9$·,
(v) —L$_B$R$_{30}$,
(w) alkanoyloxy where the alkyl group is one to twelve carbons,
(x) —OSO$_2$R$_{11}$, and
(y) —NR$_7$(X)NR$_8$·R$_9$·, R$_6$ is hydrogen or alkyl of one to twelve carbon atoms; or —L$_2$—R$_5$ and R$_6$ together are

(1)

where d is 1, 2, 3, or 4 and A is selected from
(a) —CH$_2$—,
(b) —O—,
(c) —S(O)$_r$, and
(d) —NR$_7$—, or

(2)

where the carbon-carbon double bond can be in the E or Z configuration and R$_{26}$ is selected from
(a) aryl,
(b) heterocycle,
(c) alkyl of one to twelve carbons,
(d) cycloalkyl of three to twelve carbons,
(e) cycloalkenyl of four to twelve carbons, and
(f) cycloalkenyl of four to twelve carbons where (a)–(f) can be optionally substituted with 1, 2, 3, 4, or 5 substituents independently selected from
(i) alkoxy of one to twelve carbons,
(ii) —OH, provided that no two —OH groups are attached to the same carbon,
(iii) —SH, provided that no two —SH groups are attached to the same carbon,
(iv) —CN,
(v) halo,
(vi) —CHO,
(vii) —NO$_2$,
(viii) haloalkoxy of one to twelve carbons,
(ix) perfluoroalkoxy of one to twelve carbons,
(x) —NR$_8$·R$_9$·,
(xi) =NNR$_8$·R$_9$·,
(xii) —NR$_7$NR$_8$·R$_9$·,
(Xiii) —CO$_2$R$_{10}$,
(xiv) —C(X)NR$_8$·R$_9$·,
(xv) =N—OR$_{10}$,
(xvi) =NR$_{10}$,
(xvii) —S(O)$_r$R$_{10}$,
(xviii) —X'C(X)R$_{10}$,
(xix) (=X),
(xx) —O—(CH$_2$)$_q$—Z—R$_{10}$,
(xxi) —OC(X)NR$_8$·R$_9$·,
(xxii) —L$_B$R$_{30}$,
(xxiii) alkanoyloxy where the alkyl group is one to twelve carbons,
(xxiv) —OSO$_2$R$_{11}$, and
(xxv) —NR$_7$(X)NR$_8$·R$_9$·.

3. The method according to claim 1 or 2 where
R$_1$ is hydrogen or —L$_E$—R$_E$ where L$_E$ is selected from
(1) a covalent bond,
(2) —O—,
(3) —C(O)O—,
(4) —OC(O)—, and
(5) —OC(O)O— and, R$_E$ is selected from
(1) alkyl of one to twelve carbons,
(2) alkenyl of two to twelve carbons,
(3) alkynyl of two to twelve carbons where (1)–(3) can be optionally substituted,
(4) —OH, and
(5) —NR$_7$R$_7$;

R$_2$ is H, —OH, or —O—R$_E$ where R$_E$ is alkyl of one to twelve carbons;
R$_3$ and R$_4$ are hydrogen;
L$_2$ is selected from
(1) covalent bond,
(2) alkylene of one to twelve carbons, and
(3) —NR$_7$—;

R$_5$ is selected from
(1) halo,
(2) —C(NR$_7$)OR$_{10}$,
(3) —CN,
(4) alkyl of one to twelve carbons,
(5) alkynyl of two to twelve carbons,
(6) heterocycle,
(7) aryl, and

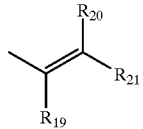

(8) where (4)–(7) and the substituents defined by R$_{19}$, R$_{20}$, and R$_{21}$ separately or together can be optionally substituted; and $R_6$ is hydrogen; or —$L_2$—$R_5$ and $R_6$ together are (=X) or

where the substituents defined by $R_{26}$ can be optionally substituted.

4. The method according to claim 1 or 2 where $R_1$ is hydrogen or O—$R_E$ where $R_E$ is selected from alkyl of one to twelve carbons;

$R_2$ is selected from hydrogen or —OH; and $R_3$, and $R_4$ are hydrogen;

$L_2$ is a covalent bond or alkylene of one to twelve carbons;

$R_5$ is aryl or 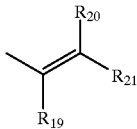

where the aryl and the substituents defined by $R_{19}$ and $R_{20}$ and $R_{21}$ separately or together can be optionally substituted;

$R_6$ is hydrogen; or $L_2$—$R_5$ and $R_6$ together are (=X).

5. The method according to claim 1 or 2 where:

$R_1$ is hydrogen or O—$R_E$ and $R_E$ is methyl;

$R_2$ is hydrogen or —OH;

$R_3$, and $R_4$ are hydrogen;

$L_2$ is selected from (1) covalent bond, and (2) alkylene of two to twelve carbons, $R_5$ is selected from (1) halo, (2) —C(=NR_7)OR_{10}, (3) —CN, (4) alkyl of one to twelve carbons, (5) alkynyl of two to twelve carbons, (6) heterocycle, (7) aryl, (8) cycloalkenyl, (9) cycloalkyl of 3 to 6 carbons, and (10)

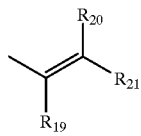

where (4)–(10) and the substituents defined by $R_{19}$, $R_{20}$ and $R_{21}$ separately or together can be optionally substituted; and $R_6$ is hydrogen; or —$L_2$—$R_5$ and $R_6$ together are (=X) or

where the substituents defined by $R_{26}$ can be optionally substituted.

6. The method according to any of claims 1, 2, 3, 4 or 5 wherein the compound is selected from 2,5-dihydro-11-methoxy-5-phenyl-2,2,4-trimethyl-1H-[1]benzopyrano[3,4-f]quinoline, 2,5-dihydro- 11-methoxy-5-(2-propenyl)-2,2,4-trimethyl-1H [1]benzopyrano[3,4-f]quinoline, 2,5-dihydro-11-methoxy-5-(3,5-dichlorophenyl)-2,2,4-trimethyl-1H-[1]benzopyrano[3,4-f]quinoline, and 2,3,5-trihydro-11-methoxy-5-(3,5-dichlorophenyl)-2,2,4-dimethyl-4-methylene-1H-[1]benzopyrano[3,4-f]quinoline.

* * * * *

UNITED STATES PATENT AND TRADEMARK OFFICE
CERTIFICATE OF CORRECTION

PATENT NO.     : 6,380,207 B2  
DATED          : April 30, 2002  
INVENTOR(S)    : Michael J. Coghlan et al.

It is certified that error appears in the above-identified patent and that said Letters Patent is hereby corrected as shown below:

<u>Title page, Item [54] and Column 1, lines 2-3,</u>  
In the title, delete "GLUCOCORTIOCOID" and insert -- GLUCOCORTICOID --, therefor.

<u>Column 25,</u>  
Line 13, delete "____" between "symbol" and "represents" and insert -- ---- --, therefor.

<u>Column 27,</u>  
Line 9, delete "$R_{7'}$ and $R_{7'}$" and insert -- $R_7$ and $R_{7'}$ --, therefor.

<u>Column 32,</u>  
Line 51, delete "——" between "symbol" and "represents" and insert -- ---- --, therefor.

<u>Column 34,</u>  
Line 16, delete "–C(X)NR$_8$R," and insert -- –C(X)NR$_8$R$_9$, --, therefor.  
Line 46, delete "=NNR$_7$R$_7$," and insert -- =NNR$_7$R$_{7'}$, --, therefor.

<u>Column 40,</u>  
Line 50, delete "–C(NR$_7$)OR$_{10}$," and insert -- –C(=NR$_7$)OR$_{10}$, --, therefor.

<u>Column 42,</u>  
Line 36, delete "2,5-dihydro- 11-methoxy-5" and insert -- 2,5-dihydro-11-methoxy-5 --, therefor.  
Line 37, delete "-1H  [1]benzopyrano" and insert -- -1H-[1]benzopyrano --, therefor.

Signed and Sealed this

Eleventh Day of March, 2003

JAMES E. ROGAN  
*Director of the United States Patent and Trademark Office*